US010787686B2

(12) United States Patent
Kaneda

(10) Patent No.: US 10,787,686 B2
(45) Date of Patent: Sep. 29, 2020

(54) METHOD FOR PRODUCING C4-DICARBOXYLIC ACID

(71) Applicant: KAO CORPORATION, Chuo-ku, Tokyo (JP)

(72) Inventor: Jitsuro Kaneda, Wakayama (JP)

(73) Assignee: Kao Corporation, Tokyo (JP)

( * ) Notice: Subject to any disclaimer, the term of this patent is extended or adjusted under 35 U.S.C. 154(b) by 58 days.

(21) Appl. No.: 15/767,808

(22) PCT Filed: Oct. 27, 2016

(86) PCT No.: PCT/JP2016/081796
§ 371 (c)(1),
(2) Date: Apr. 12, 2018

(87) PCT Pub. No.: WO2017/073640
PCT Pub. Date: Apr. 5, 2017

(65) Prior Publication Data
US 2018/0327791 A1    Nov. 15, 2018

(30) Foreign Application Priority Data

Oct. 28, 2015   (JP) ................... 2015-211884
Oct. 28, 2015   (JP) ................... 2015-211885

(51) Int. Cl.
| | | |
|---|---|---|
| C12N 1/15 | (2006.01) | |
| C12N 1/21 | (2006.01) | |
| C12P 7/46 | (2006.01) | |
| C12N 15/80 | (2006.01) | |
| C07K 14/37 | (2006.01) | |
| C12N 15/09 | (2006.01) | |

(52) U.S. Cl.
CPC ............. *C12P 7/46* (2013.01); *C07K 14/37* (2013.01); *C12N 15/09* (2013.01); *C12N 15/80* (2013.01)

(58) Field of Classification Search
None
See application file for complete search history.

(56) References Cited

U.S. PATENT DOCUMENTS

2014/0127767 A1* 5/2014 Ma .................... C07C 5/142
                                                435/145
2018/0291406 A1   10/2018 Kaneda

FOREIGN PATENT DOCUMENTS

| CN | 103013843 A | 4/2013 | |
|---|---|---|---|
| EP | 2495304 A1 * | 9/2012 | ............... C12N 9/88 |
| JP | 2017-075097 A | 4/2017 | |
| JP | 2017-79644 A | 5/2017 | |
| JP | 2017-79645 A | 5/2017 | |
| WO | WO 2017/065167 A1 | 4/2017 | |

OTHER PUBLICATIONS

Guo et al., Protein tolerance to random amino acid change, Proc. Natl. Acad. Sci. USA, 2004, 101, 9205-10.*
Moon et al., Metabolic engineering of *Escherichia coli* for the production of malic acid, Biochem. Eng. J., 2008, 40, 312-20.*
Uniprot, Accession No. I1BPG4, 2015, www.uniprot.org.*
Uniprot, Accession No. I1C123, 2016, www.uniprot.org.*
Straathof et al., Chapter 11: Production of Fumaric Acid by Fermentation, in Reprogramming Microbial Metabolic Pathways, X. Wang et al. (eds.), 2012. 223-40.*
Skory et al., Native and modified lactate dehydrogenase expression in a fumaric acid producing isolate Rhizopus oryzae 99-880, Curr. Genet., 2007, 52, 23-33.*
Ma et al., Genomic Analysis of the Basal Lineage Fungus Rhizopus oryzae Reveals a Whole-Genome Duplication, PLoS genetic, 2009, 5, e1000549.*
GenBank, Accession No. CH476733.1, Mar. 2015, www.ncbi.nlm.nih.gov.*
Zhang et al., Metabolic engineering of Rhizopus oryzae, Process Biochem., 2012, 47, 2159-65.*
Uniprot, Accession No. I1C123, 2015, www.uniprot.org.*
International Search Report (ISR) for PCT/JP2016/081796; I.A. fd Oct. 27, 2016, dated Jan. 31, 2017 from the Japan Patent Office, Tokyo, Japan.
International Preliminary Report on Patentability (IPRP), Chapter I of the Patent Cooperation Treaty, including the Written Opinion for PCT/JP2016/081796;I.A. fd Oct. 27, 2016, dated May 1, 2018, by the International Bureau of WIPO, Geneva, Switzerland.
Zhang, B. et al., "Metabolic engineering of *Rhizopus oryzae*: Effects of overexpressing pyc and pepc genes on fumaric acid biosynthesis from glucose," Metab Eng. Sep. 2012;14(5):512-20. doi: 10.1016/j.ymben.2012.07.001. Epub Jul. 17, 2012, Academic Press, Orlando, FL.
Ma, L.-J. et al., "Genomic analysis of the basal lineage fungus *Rhizopus oryzae* reveals a whole-genome duplication," PLoS Genet. Jul. 2009;5(7):e1000549. doi: 10.1371/journal.pgen.1000549. Epub Jul. 3, 2009, 11 pages, Public Library of Science, San Francisco, CA.
Horn, F. et al., "Draft Genome Sequences of Symbiotic and Nonsymbiotic *Rhizopus microsporus* Strains CBS 344.29 and ATCC 62417," Genome Announc. Jan. 22, 2015;3(1). pii: e01370-14. doi: 10.1128/genomeA.01370-14, 2 pages, American Society for Microbiology, Washington, DC.
Database GenBank [online], (excerpt) Accession No. CH476733.1, Mar. 23, 2015, [retrieval date Jan. 18, 2017], Rhizopus oryzae RA 99-880 supercont3.2 genomic scaffold, whole genome shotgun sequence, locus_tag=RO3G_02779, RO3G_02798, 5 pages.

(Continued)

*Primary Examiner* — Robert B Mondesi
*Assistant Examiner* — Todd M Epstein
(74) *Attorney, Agent, or Firm* — Sterne, Kessler, Goldstein & Fox P.L.L.C.

(57) ABSTRACT

Provided is a transformed cell improved in C4 dicarboxylic acid productivity. A transformed cell containing a foreign polynucleotide encoding a polypeptide consisting of an amino acid sequence represented by SEQ ID NO: 2, an amino acid sequence represented by SEQ ID NO: 22 or an amino acid sequence having an identity of at least 80% with any of the sequences.

15 Claims, No Drawings
Specification includes a Sequence Listing.

(56) References Cited

OTHER PUBLICATIONS

Database GenBank [online], (excerpt) Accession No. CH476736.1, Mar. 23, 2015, [retrieval date Jan. 18, 2017], Rhizopus oryzae RA 99-880 supercont3.5 genomic scaffold, whole genome shotgun sequence, locus_tag=RO3G_06858, 3 pages.

Database GenBank [online], Accession No. CDGI01000004.1, Nov. 29, 2014, [retrieval date Jan. 18, 2017], Rhizopus microsporus genome assembly Rmicro_CBS_344.29_Allpaths-LG, scaffold SCAF4, whole genome shotgun sequence, locus_tag=RMCBS344292_00272, 77 pages.

Database GenBank [online], Accession No. CDGI01001026.1, Nov. 29, 2014, [retrieval date Jan. 18, 2017], Rhizopus microsporus genome assembly Rmicro_CBS_344.29_Allpaths-LG, scaffold SCAF1026, whole genome shotgun sequence, locus_tag=RMCBS344292_18117, 6 pages.

Database GenBank [online], Accession No. CCYT01000317.1, Apr. 9, 2015, [retrieval date Jan. 18, 2017], Rhizopus microsporus genome assembly RMATCC62417_Allpaths-LG, scaffold SCAF317, whole genome shotgun sequence, locus_tag=RMATCC62417_16085, 8 pages.

Database GenBank [online], (excerpt) Accession No. CCYT01000002.1, Apr. 9, 2015, [retrieval date Jan. 18, 2017], Rhizopus microsporus genome assembly RMATCC62417_Allpaths-LG, scaffold SCAF2, whole genome shotgun sequence, locus_tag=RMATCC62417_01123, 3 pages.

* cited by examiner

METHOD FOR PRODUCING C4-DICARBOXYLIC ACID

REFERENCE TO SEQUENCE LISTING SUBMITTED ELECTRONICALLY

The content of the electronically submitted substitute sequence listing, file name 2537_1500002_SL.txt, size 19,827 bytes; and date of creation Jul. 27, 2018, filed herewith, is incorporated herein by reference in its entirety.

FIELD OF THE INVENTION

The present invention relates to a biological production of a C4 dicarboxylic acid.

BACKGROUND OF THE INVENTION

C4 dicarboxylic acids are used not only for various applications in the food industry, as an acidulant, an antimicrobial agent and a pH modifier, but also as a raw material for synthetic resins and biodegradable polymers, and are industrially variable substances. Industrially, C4 dicarboxylic acids are produced by either chemical synthesis from petrochemical raw materials or microbial fermentation. Conventionally, a chemical synthesis method has been dominantly used because its lower cost; however, recently, in view of e.g., a sharp increase in material cost and environmental load, the production method by microbial fermentation using a recyclable resource as a raw material has attracted attention.

Fumaric acid, one of the C4 dicarboxylic acids, is known to be produced using a fermentative fungus such as *Rhizopus*. *Rhizopus* utilizes glucose as a carbon source to produce fumaric acid and excretes it to the outside of the cell. To date, regarding techniques for increasing production of fumaric acid by *Rhizopus*, for example, improvement in a culture method and preparation of a highly productive strain by mutation breeding are known. However, genetic background of *Rhizopus* has not yet been sufficiently studied and thus, it is not easy to develop a technology for improved production of a fumaric acid by *Rhizopus* through genetic recombination, and the number of reports is few. It is only reported that fumaric acid productivity is improved by introducing a gene encoding pyruvate carboxylase and derived from *Saccharomyces cerevisiae*, in *Rhizopus delemar* (Patent Literature 1); and introducing a gene encoding phosphoenolpyruvate carboxylase and derived from *Escherichia coli* in *Rhizopus oryzae* (Non Patent Literature 1). (Patent Literature 1) Chinese Patent Publication No. CN103013843 (Non Patent Literature 1) Metabolic Engineering, 2012, 14: 512-520,

SUMMARY OF THE INVENTION

The present invention provides a transformed cell comprising an exogenous polynucleotide encoding a polypeptide consisting of an amino acid sequence represented by SEQ ID NO: 2, an amino acid sequence represented by SEQ ID NO: 22 or an amino acid sequence having an identity of at least 80% with any of the sequences.

The present invention provides a method for producing a C4 dicarboxylic acid, comprising culturing the transformed cell mentioned above.

The present invention provides a method for producing a transformed cell, comprising introducing a polynucleotide encoding a polypeptide consisting of an amino acid sequence represented by SEQ ID NO: 2, an amino acid sequence represented by SEQ ID NO: 22 or an amino acid sequence having an identity of at least 80% with any of the sequences, or a vector containing the polynucleotide into a host cell.

The present invention further provides a method for improving C4 dicarboxylic acid productivity in a host cell, comprising introducing a polynucleotide encoding a polypeptide consisting of an amino acid sequence represented by SEQ ID NO: 2, an amino acid sequence represented by SEQ ID NO: 22 or an amino acid sequence having an identity of at least 80% with any of the sequences, or a vector containing the polynucleotide into a host cell.

DETAILED DESCRIPTION OF THE INVENTION

The present invention relates to a polypeptide having an effect of improving C4 dicarboxylic acid productivity on a host cell, a gene encoding the polypeptide, a transformed cell containing the gene and a method for producing a C4 dicarboxylic acid using the transformed cell.

As a result of intensive studies, the present inventors found that when expression of a polypeptide consisting of the amino acid sequence represented by SEQ ID No: 2 or SEQ ID No: 22 is enhanced in a cell, C4 dicarboxylic acid productivity in the cell can be improved.

The present invention provides a polypeptide having a function to improve C4 dicarboxylic acid productivity in a cell and a transformed cell enhanced in expression of the polypeptide (for example, a cell in which a gene encoding the polypeptide is introduced). The transformed cell of the present invention can produce a larger amount of a C4 dicarboxylic acid. Accordingly, the transformed cell of the present invention is useful for biological production of a C4 dicarboxylic acid. The features and advantages of the present invention mentioned above will be more clearly understood based on the following description of the specification.

1. Definition

In the specification, an identity of amino acid sequences or nucleotide sequences can be calculated in accordance with the Lipman-Pearson method (Science, 1985, 227: 1435-1441). More specifically, the identity can be analyzed based on the homology analysis program of genetic information processing software GENETYCS Ver. 12 (i.e., amino acid sequence×amino acid sequence maximum matching or nucleotide sequence×nucleotide sequence maximum matching) and by assigning −1 to Maches, 1 to Mismatches, 1 to Gaps and *N+2.

In the specification, "an identity of at least 80%" regarding an amino acid sequence or a nucleotide sequence refers to an identity of 80% or more, preferably 85% or more, more preferably 90% or more, further preferably 95% or more, still further preferably 96% or more, further more preferably 97% or more, further more preferably 98% or more and further more preferably 99% or more.

In the specification, "the corresponding region" of an amino acid sequence or a nucleotide sequence can be determined by aligning a sequence of interest and a reference sequence (for example, the amino acid sequence represented by SEQ ID No: 2) so as to obtain a maximum homology. Amino acid sequences or nucleotide sequences can be aligned by use of an algorithm known in the art and the procedure thereof is known to those skilled in the art. For example, the alignment can be manually made based on e.g., the Lipman-Pearson method mentioned above, or alternatively, based on Clustal W multiple alignment program (Thompson, J. D. et al, 1994, Nucleic Acids Res. 22: 4673-4680) by default. Clustal W can be used on the website of, for example, the European Bioinformatics Laboratory (European Bioinformatics Institute: EBI [www.ebi.ac.uk/index.html]) or the Japan DNA Data Bank (MBJ[www.ddbj.nig.ac.jp/Welcome-j.html]) managed by the National Institute of Genetics. The region of the sequence of interest aligned with an optional region of a reference sequence by the alignment operation is regarded as "the corresponding region" to the optional region.

In the specification, the "amino acid sequence having deletion, substitution, addition or insertion of one or more amino acids" refers to an amino acid sequence having deletion, substitution, addition or insertion of 1 or more and 10 or less, preferably 1 or more and 8 or less, more preferably 1 or more and 5 or less and further preferably 1 or more and 3 or less amino acid(s). In the specification, the "nucleotide sequence having deletion, substitution, addition or insertion of one or a plurality of nucleotides" refers to a nucleotide sequence having deletion, substitution, addition or insertion of 1 or more and 30 or less, preferably 1 or more and 24 or less, more preferably 1 or more and 15 or less and still further preferably 1 or more and 9 or less nucleotide(s). In the specification, "addition" of an amino acid or a nucleotide includes addition of the amino acid or the nucleotide to one and both ends of a sequence.

In the specification, "upstream" and "downstream" regarding to a gene refer to upstream and downstream of the gene in the transcriptional orientation. For example, "a gene arranged downstream of a promoter" means that the gene is present on the 3' side of the promoter in a DNA sense strand and the upstream of a gene means the region on the 5' side of the gene in the DNA sense strand.

In the specification, the "operable linking" between a regulatory region and a gene refers to the linking of the gene to the regulatory region such that the gene can be expressed under control of the regulatory region. A procedure for "operable linking" between a gene and a regulatory region is well known to those skilled in the art.

In the specification, the term "intrinsic" used for function, property and trait of a cell means that the function, property and trait are present in the cell of a wild type. In contrast, the term "exogenous" is used for representing that the function, property and trait are not originally present in a cell but externally introduced in the cell. For example, an "exogenous" gene or polynucleotide is a gene or polynucleotide introduced in a cell from the outside. The exogenous gene or polynucleotide may be derived from the same biological species as a recipient cell or a different biological species (more specifically, heterologous gene or polynucleotide).

In the specification, "C4 dicarboxylic acid productivity" of a cell is represented as a yield (%) of a C4 dicarboxylic acid in a culture medium of the cell; more specifically, mass (%) of an amount of the C4 dicarboxylic acid produced by the cell relative to an amount of a carbon source consumed in the culture medium of the cell. The amount of a C4 dicarboxylic acid produced by a cell can be computationally obtained as the amount of the C4 dicarboxylic acid in the culture supernatant, which is obtained by removing cells from a cultured broth of the cells. The amount of a carbon source consumed in the culture medium can be calculated by subtracting the amount of a carbon source in the culture supernatant from the initial concentration of the carbon source in the culture medium. The amounts of a C4 dicarboxylic acid and carbon source in the culture supernatant can be measured by e.g., high-speed liquid chromatography (HPLC). The measurement procedure will be more specifically described later in Reference Example 1.

In the specification, "improvement of C4 dicarboxylic acid productivity" in a transformed cell means that C4 dicarboxylic acid productivity of the transformed cell is improved compared to that of a host cell or a control cell. The improvement rate of C4 dicarboxylic acid productivity in a transformed cell is calculated in accordance with the following expression:

Improvement rate (%)=(C4 dicarboxylic acid productivity in a transformed cell/C4 dicarboxylic acid productivity of host cell or control cell)× 100−100

The transformed cell herein refers to a cell enhanced in expression of the polypeptide of the present invention, for example, a cell in which a polynucleotide encoding the polypeptide of the present invention or a vector containing the polynucleotide is introduced. The host cell refers to a host cell (a parent cell) for the transformed cell. The control cell refers to a cell in which a vector not containing a polynucleotide encoding the polypeptide of the present invention is introduced. Preferably, the improvement rate of C4 dicarboxylic acid productivity is calculated based on the C4 dicarboxylic acid productivity of the transformed cell at a maximum time point of C4 dicarboxylic acid concentration in the culture supernatant (containing no cells) of the transformed cell. Accordingly, in the specification, "a transformed cell improved in C4 dicarboxylic acid productivity by X % or more" refers to a transformed cell exhibiting an improvement rate of C4 dicarboxylic acid productivity, calculated in accordance with the above expression, of X % or more. The "improvement of C4 dicarboxylic acid productivity by X % or more" in a cell means that the improvement rate of C4 dicarboxylic acid productivity of the cell, calculated in accordance with the above expression, is X % or more.

Examples of the C4 dicarboxylic acid to be produced by the present invention include fumaric acid, malic acid and succinic acid, and fumaric acid is preferable.

In the specification, a "multiple transmembrane polypeptide" refers to a transmembrane polypeptide predicted to have a plurality of transmembrane helix structures based on an analysis using a cell transmembrane region prediction program. Examples of the cell transmembrane region prediction program include analysis programs using a prediction method such as TMHMM Server, v. 2.0 (Journal of Molecular Biology, 2001, 305: 567-580), DAS-TMfilter (Protein Eng., 2002, Volume 15, Issue 9: 745-752) and PRED-TMR2 (Protein Eng., 1999, Volume 12, Issue 8: 631-634).

2. Transformed Cell Improved in C4 Dicarboxylic Acid Productivity

The present inventors found that when a polynucleotide encoding a polypeptide consisting of an amino acid sequence represented by SEQ ID NO: 2 or SEQ ID NO: 22 is introduced in a cell, C4 dicarboxylic acid productivity in the cell can be improved. Accordingly, the polypeptide consisting of an amino acid sequence represented by SEQ ID NO: 2 or SEQ ID NO: 22 or a polypeptide having the same function as in either one of these (hereinafter sometimes collectively referred tows "the polypeptide of the present invention") is predicted to have a function to improve C4 dicarboxylic acid productivity.

Accordingly, in an embodiment, the present invention provides a transformed cell improved in C4 dicarboxylic acid productivity. In a preferable embodiment, the transformed cell of the present invention is a cell containing an exogenous polynucleotide encoding a polypeptide consisting of an amino acid sequence represented by SEQ ID NO: 2, a polypeptide consisting of an amino acid sequence represented by SEQ ID NO: 22 or a polypeptide having the same function of either one of these. In another embodiment, the transformed cell of the present invention is a cell obtained by modifying a host cell containing a polynucleotide encoding a polypeptide consisting of an amino acid sequence represented by SEQ ID NO: 2, a polypeptide consisting of an amino acid sequence represented by SEQ. ID NO: 22 or a polypeptide having the same function of either one of these as a gene on a genome thereof such that the regulatory region of the gene is modified so as to improve the transcript amount of the gene.

A polypeptide consisting of an amino acid sequence represented by SEQ ID NO: 2 is a protein unknown in function and derived from *Rhizopus delemar* RA 99-880 (accession number: RO3G_02798). As a result of an analysis using a cell transmembrane region prediction program, TMHMM Server, v. 2.0, a polypeptide consisting of an amino acid sequence represented by SEQ ID NO: 2 had a transmembrane helix structure in each of the 53rd to 75th, 90th to 112th, 119th to 141st, 145th to 167th, 180th to 198th, 208th to 230th, 243rd to 265th, 275th to 294th, 315th to 337th, 347th to 369th, 376th to 398th, 408th to 430th, 443rd to 465th and 511th to 533rd amino acid regions of the amino acid sequence and was predicted as a 14 transmembrane polypeptide. Accordingly, the polypeptide consisting of an amino acid sequence represented by SEQ ID NO: 2 is predicted to be a multiple transmembrane polypeptide. In consideration of the fact that a transporter polypeptide having an activity to transport a substance inside and outside the cell membrane usually has a multiple transmembrane structure, it is predicted that the polypeptide is a transporter-like polypeptide.

As the polypeptide having the same function as in the polypeptide consisting of an amino acid sequence represented by SEQ ID NO: 2, a polypeptide consisting of an amino acid sequence having an identity of at least 80% with the amino acid sequence represented by SEQ ID NO: 2 is mentioned. In a preferable embodiment, the polypeptide is a multiple transmembrane polypeptide consisting of an amino acid sequence having an identity of at least 80% with the amino acid sequence represented by SEQ ID NO: 2 and having 14 transmembrane helix structures. In a more preferable embodiment, the polypeptide is a multiple transmembrane polypeptide consisting of an amino acid sequence having an identity of at least 80% with the amino acid sequence represented by SEQ ID NO: 2 and having a transmembrane helix structure in each of the corresponding regions to the 53rd to 75th, 90th to 112th, 119th to 141st, 145th to 167th, 180th to 198th, 208th to 230th, 243rd to 265th, 275th to 294th, 315th to 337th, 347th to 369th, 376th to 398th, 408th to 430th, 443rd to 465th and 511th to 533rd amino acid regions of the amino acid sequence represented by SEQ ID NO: 2.

Examples of the amino acid sequence having an identity of at least 80% with the amino acid sequence represented by SEQ ID No: 2 include an amino acid sequence having deletion, substitution, addition or insertion of one or a plurality of amino acids with respect to the amino acid sequence represented by SEQ ID No: 2.

The polypeptide consisting of an amino acid sequence represented by SEQ ID NO: 22 is a protein unknown in function and derived from *Rhizopus delemar* RA 99-880 (accession number: RO3G_06858). As a result of an analysis using a cell transmembrane region prediction program, TMHMM Server, v. 2.0, the polypeptide consisting of an amino acid sequence represented by SEQ ID NO: 22 had a transmembrane helix structure in each of the 13th to 32nd, 42nd to 64th, 71st to 93rd, 97th to 119th, 131st to 153rd, 163rd to 182nd, 189th to 206th and 212th to 234th amino acid regions of the amino acid sequence and was predicted as an eight transmembrane polypeptide. Accordingly, the polypeptide consisting of an amino acid sequence represented by SEQ ID NO: 22 is predicted to be a multiple transmembrane polypeptide. In consideration of the fact that a transporter polypeptide having an activity to transport a substance inside and outside the cell membrane usually has a multiple transmembrane structure, it is predicted that the polypeptide is a transporter-like polypeptide.

As a polypeptide having the same function as that in the polypeptide consisting of an amino acid sequence represented by SEQ ID NO: 22, a polypeptide consisting of an amino acid sequence having an identity of at least 80% with the amino acid sequence represented by SEQ ID NO: 22 is mentioned. In a preferable embodiment, the polypeptide is a multiple transmembrane polypeptide consisting of an amino acid sequence having an identity of at least 80% with the amino acid sequence represented by SEQ ID NO: 22 and having 8 transmembrane helix structures. In a more preferable embodiment, the polypeptide is a multiple transmembrane polypeptide consisting of an amino acid sequence having an identity of at least 80% with the amino acid sequence represented by SEQ ID NO: 22 and having a transmembrane helix structure in each of the corresponding regions to the 13th to 32nd, 42nd to 64th, 71st to 93rd, 97th to 119th, 131st to 153rd, 163rd to 182nd, 189th to 206th and 212th to 234th amino acid regions of the amino acid sequence represented by SEQ ID NO: 22.

Examples of the amino acid sequence having an identity of at least 80% with the amino acid sequence represented by SEQ ID NO: 22 include an amino acid sequence having deletion, substitution, addition or insertion of one or a plurality of amino acids with respect to the amino acid sequence represented by SEQ ID NO: 22.

As a method of introducing a mutation such as deletion, substitution, addition or insertion of an amino acid(s) in an amino acid sequence, for example, a method of introducing a mutation such as deletion, substitution, addition or insertion of a nucleotide(s) in the nucleotide sequence encoding the amino acid sequence, is mentioned. Examples of a technique of introducing a mutation in a nucleotide sequence, include mutagenesis with a chemical mutagen such as ethyl methanesulfonate, N-methyl-N-nitrosoguanidine and nitrous acid, or a physical mutagen such as an ultraviolet ray, X ray, gamma ray and an ion beam, a site-specific mutagenesis and a method described in Dieffenbach et al. (Cold Spring Harbor Laboratory Press, New York, 581-621, 1995). Examples of the site-specific mutagenesis method include a method using Splicing overlap extension (SOE) PCR (Horton et al., Gene 77, 61-68, 1989), ODA method (Hashimoto-Gotoh et al., Gene, 152, 271-276, 1995) and Kunkel method (Kunkel, T. A., Proc. Natl. Acad. Sci. USA, 1985, 82, 488). Alternatively, a commercially available kit for site-specific mutagenesis such as Site-Directed Mutagenesis System Mutan-SuperExpress Km kit (Takara Bio Inc.), Transformer™ Site-Directed Mutagenesis kit (Clontech) and KOD-Plus-Mutagenesis Kit (Toyobo Co., Ltd.), can be used.

As the exogenous polynucleotide encoding the polypeptide of the present invention and to be contained in the transformed cell of the present invention, a polynucleotide consisting of a nucleotide sequence represented by SEQ ID NO: 1 or a nucleotide sequence having an identity of at least 80% with the nucleotide sequence may be mentioned. In a preferable embodiment, the polynucleotide encodes a polypeptide consisting of the amino acid sequence represented by SEQ ID No: 2 or a multiple transmembrane polypeptide consisting of an amino acid sequence having an identity of at least 80% with any of the sequences and having fourteen transmembrane helix structures. In a more preferable embodiment, the polynucleotide encodes a polypeptide consisting of an amino acid sequence represented by SEQ ID NO: 2 or a multiple transmembrane polypeptide consisting of an amino acid sequence having an identity of at least 80% with any of the sequences and having a transmembrane helix structure in each of the corresponding regions to the 53rd to 75th, 90th to 112th, 119th to 141st, 145th to 167th, 180th to 198th, 208th to 230th, 243rd to 265th, 275th to 294th, 315th to 337th, 347th to 369th, 376th to 398th, 408th to 430th, 443rd to 465th and 511th to 533rd amino acid regions of the amino acid sequence represented by SEQ ID NO: 2.

As the exogenous polynucleotide encoding the polypeptide of the present invention and to be contained in the transformed cell of the present invention, a polynucleotide consisting of a nucleotide sequence represented by SEQ ID NO: 21 or a nucleotide sequence having an identity of at least 80% with the nucleotide sequence may be mentioned. In a preferable embodiment, the polynucleotide encodes a polypeptide consisting of an amino acid sequence represented by SEQ ID NO: 22 or a multiple transmembrane polypeptide consisting of an amino acid sequence having an identity of at least 80% with any of the sequences and having 8 transmembrane helix structures. In a more preferable embodiment, the polynucleotide encodes the polypeptide consisting of an amino acid sequence represented by SEQ ID NO: 22 or a multiple transmembrane polypeptide consisting of an amino acid sequence having an identity of at least 80% with any of the sequences and having a transmembrane helix structure in each of the corresponding regions to the 13th to 32nd, 42nd to 64th, 71st to 93rd, 97th to 119th, 131st to 153rd, 163rd to 182nd, 189th to 206th and 212th to 234th amino acid regions of the amino acid sequence represented by SEQ ID NO: 22.

Examples of the nucleotide sequence having an identity of at least 80% with the nucleotide sequence represented by SEQ ID No: 1 include a nucleotide sequence having deletion, substitution, addition or insertion of one or a plurality of nucleotides with respect to the nucleotide sequence represented by SEQ ID No: 1. Examples of the nucleotide sequence having an identity of at least 80% with the nucleotide sequence represented by SEQ ID NO: 21, include a nucleotide sequence having deletion, substitution, addition or insertion of one or a plurality of nucleotides with respect to the nucleotide sequence represented by SEQ ID NO: 21. As a method of introducing a mutation such as a deletion, substitution, addition or insertion of a nucleotide(s) in a nucleotide sequence, for example, the same methods mentioned above are employed. The polynucleotide to be contained in the transformed cell of the present invention may be a single strand or double strand; or either DNA or RNA. The DNA may be cDNA and an artificial DNA such as a chemically synthesized DNA.

In the transformed cell of the present invention, the polynucleotide encoding the polypeptide of the present invention may be integrated in a vector. The vector containing the polynucleotide is preferably an expression vector. The vector is preferably an expression vector, through which the polynucleotide can be introduced into a host cell and the polynucleotide can be expressed in the host cell. The vector preferably contains the polynucleotide encoding the polypeptide of the present invention and a regulatory region operably linked to the polynucleotide. The vector may be a vector capable of extrachromosomally and autonomously proliferating and replicating such as a plasmid, or a vector intrachromosomally integrated.

Examples of the vector include pBluescript II SK (−) (Stratagene), a pUC vector such as pUC18 (Takara Bio Inc.), a pET vector (Takara Bio Inc.), a pGEX vector (GE healthcare), a pCold vector (Takara Bio Inc.), a pHY300PLK (Takara Bio Inc.), pUB110 (Mckenzie, T. et al., 1986, Plasmid 15 (2): 93-103), pBR322 (Takara Bio Inc.), pRS403 (Stratagene), pMW218/219 (Nippon Gene Co., Ltd.), a pRI vector (Takara Bio Inc.), a pBI vector (Clontech) and an IN3 vector (Inplanta Innovations Inc.).

In the transformed cell of the present invention, the polynucleotide encoding the polypeptide of the present invention may be DNA integrated in genomic DNA. In this case, a DNA fragment containing the polynucleotide encoding the polypeptide of the present invention may be constructed and introduced into a host cell. As the DNA fragment, for example, a DNA fragment amplified by PCR and a DNA fragment digested by a restriction enzyme, may be mentioned. The DNA fragment may be an expression cassette containing the polynucleotide encoding the polypeptide of the present invention and a regulatory region operably linked thereto.

The regulatory region to be contained in a vector or a DNA fragment is a sequence for expressing the polynucleotide encoding the polypeptide of the present invention within a host cell to which the vector or DNA fragment is to be introduced, for example, an expression regulatory region such as a promoter and a terminator, and an origin of replication, are mentioned. The type of the regulatory region can be appropriately selected depending upon the type of host cell to which a vector or a DNA fragment is to be introduced. If necessary, the vector or DNA fragment may further have a selection marker such as an antibiotic resistant gene and amino acid synthesis related genes.

The transformed cell of the present invention can be obtained by introducing a vector or DNA fragment containing the polynucleotide encoding the polypeptide of the present invention into a host cell. This is a transformed cell containing a vector or an exogenous DNA fragment containing the polynucleotide encoding the polypeptide of the present invention. Alternatively, in the case where a host cell has the polynucleotide encoding the polypeptide of the present invention as a gene on the genome thereof, the transformed cell of the present invention can be obtained by modifying the regulatory region of the gene to improve the transcript amount of the gene in the host cell. In the transformed cell of the present invention, the transcript amount of the gene encoding the polypeptide of the present invention compared to the host cell (parent cell) increases. The transcript amount of the gene can be determined based on measurement of mRNA amount by quantification PCR, RNA-Seq analysis using a next generation sequencer, DNA microarray analysis and the like.

As the host cell for the transformed cell, any one of a microbial cell, a plant cell and an animal cell may be used.

In view of production efficiency of a C4 dicarboxylic acid, the host cell is preferably a microbial cell. The microbe may be either a prokaryote or a eukaryote. Of these microbes, in view of C4 dicarboxylic acid productivity, a filamentous fungus or a yeast is preferable and a filamentous fungus is more preferable. Examples of the filamentous fungus include all filamentous fungi belonging to subdivisions, Eumycota and Oomycota (as defined by Hawksworth et al., In, Ainsworth and Bisby's Dictionary of The Fungi, 8th edition, 1995, CAB International, University, Press, Cambridge, UK). A filamentous fungus is generally characterized by a mycelial wall constituted of chitin, cellulose, glucan, chitosan, mannan or another polysaccharide conjugate. Vegetative growth is made by extension of hyphae and carbon is metabolized in absolute aerobic conditions.

Preferable examples of the filamentous fungus to be used as a host cell for the transformed cell of the present invention include filamentous fungi of the genus *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Parasitella, Penicillium, Phanerochaete, Phlebia, Piromyces, Pleurotus, Rhizopus, Schizophyllum, Talaromyces, Thermoascus, Thielavia, Tolypocladium, Trametes* and *Trichoderma*. Of these, in view of C4 dicarboxylic acid productivity, filamentous fungi of the genus *Rhizopus* such as *Rhizopus delemar, Rhizopus arrhizus, Rhizopus chinensis, Rhizopus nigricans, Rhizopus tonkinensis, Rhizopus tritici* and *Rhizopus oryzae* are preferable; *Rhizopus delemar* and *Rhizopus oryzae* are more preferable; and *Rhizopus delemar* is further preferable.

In introducing a vector or a DNA fragment in the host cell, a general transformation method such as an electroporation method, a transformation method, a transfection method, a conjugation method, a protoplast method, a particle-gun method and an *agrobacterium* method, can be used.

A transformed cell having a desired vector or DNA fragment introduced therein can be selected by using a selection marker. For example, when the selection marker is an antibiotic resistant gene, the transformed cell having a desired vector or DNA fragment introduced therein can be obtained culturing the cell in the medium containing the antibiotic. When the selection marker is, for example, an amino acid synthesis related gene, the gene may be introduced into a host cell which is the amino acid-auxotrophic. A transformed cell having a desired vector or DNA fragment introduced therein can be selected based on whether the cell is amino acid auxotrophic or not. Alternatively, introduction of a desired vector or DNA fragment can be confirmed by examining the DNA sequence of the transformed cell by e.g., PCR.

A transformed cell of the present invention is improved in transcript amount of the polynucleotide encoding the polypeptide of the present invention and enhanced in expression of the polypeptide of the present invention. Owing to this, the transformed cell is improved in C4 dicarboxylic acid productivity. The C4 dicarboxylic acid productivity of the transformed cell, compared to a host cell (a parent cell) thereof, is improved by preferably 10% or more, more preferably 15% or more, and further preferably 20% or more.

3. Production of a C4 Dicarboxylic Acid

The transformed cell of the present invention is improved in C4 dicarboxylic acid productivity. Accordingly, the present invention also provides a method for producing a C4 dicarboxylic acid, including culturing the transformed cell of the present invention. As the C4 dicarboxylic acid to be produced by the production method of the present invention, fumaric acid, malic acid and succinic acid are mentioned and preferably fumaric acid is mentioned.

Cultivation of a transformed cell in the production method of the present invention includes culturing a microbe, a plant, an animal or a cell or tissue thereof containing the transformed cell. The medium and culture conditions for culturing the transformed cell can be appropriately selected depending upon the type of host for the transformed cell. Usually, a medium and culture condition routinely used for a host for the transformed cell can be employed.

For example, when the transformed cell is a filamentous fungus cell, the culture temperature may be, for example, from 10° C. to 50° C., and preferably from 25° C. to 45° C.; the culture period, which is not particularly limited as long as it is the period during which a desired C4 dicarboxylic acid is sufficiently produced, may be, for example, from 1 to 240 hours, preferably from 12 to 120 hours and preferably from 24 to 72 hours. Cultivation is preferably carried out while stirring or under aeration.

As a medium for culturing a filamentous fungus, a medium routinely used may be used. The medium is preferably a liquid medium and any one of a synthesis medium, a natural medium, and a semisynthetic medium in which a natural component is added to a synthesis medium, may be used. A commercially available medium such as PDB medium (potato dextrose medium, manufactured by e.g., Becton, Dickinson and Company), PDA medium (manufactured by e.g., Becton, Dickinson and Company, LB medium (Luria-Bertani medium, manufactured by e.g., Nihon Pharmaceutical Co., Ltd. (brand name e.g., "DAIGO")), NB medium (Nutrient Broth, manufactured by e.g., Becton, Dickinson and Company), SB medium (Sabouraud medium, manufactured by e.g., OXOID Ltd.) and SD medium (Synthetic Dropout Broth; for example, Clontech), can be used. The medium usually contains e.g., a carbon source, a nitrogen source and an inorganic salt; however, each component composition can be appropriately selected.

Now, the composition of a preferable medium for culturing a filamentous fungus will be more specifically described, below. The concentrations of individual components in the medium described below represent initial concentrations thereof (at the time of preparation of a medium or at the time of starting culture).

Examples of the carbon source in a medium as mentioned above include glucose, maltose, starch hydrolysate, fructose, xylose and sucrose. Of them, glucose and fructose are preferable. These sugars can be used alone or in combination of two or more. The concentration of the carbon source in a medium is preferably 1% (w/v) or more and more preferably 5% (w/v) or more; and preferably 400 (w/v) or less and more preferably 30% (w/v) or less. In short, the concentration of the carbon source in a medium is preferably from 1 to 40% (w/v) and more preferably 5 to 30% (w/v).

Examples of the nitrogen source in a medium include a nitrogen-containing compound such as ammonium sulfate, urea, ammonium nitrate, potassium nitrate and sodium nitrate. The concentration of the nitrogen source in a medium is preferably from 0.001 to 0.5% (w/v) and more preferably from 0.001 to 0.2% (w/v).

The medium can contain e.g., a sulfate, a magnesium salt and a zinc salt. Examples of the sulfate include magnesium sulfate, zinc sulfate, potassium sulfate, sodium sulfate and ammonium sulfate. Examples of the magnesium salt include magnesium sulfate, magnesium nitrate and magnesium chloride. Examples of the zinc salt include zinc sulfate, zinc nitrate and zinc chloride. The concentration of the sulfate in a medium is preferably from 0.01 to 0.5% (w/v) and more preferably from 0.02 to 0.2% (w/v). The concentration of the magnesium salt in a medium is preferably from 0.001 to 0.5% (w/v) and more preferably from 0.01 to 0.1% (w/v). The concentration of the zinc salt in a medium is preferably from 0.001 to 0.05% (w/v) and more preferably from 0.005 to 0.05% (w/v).

The pH (25° C.) of a medium is preferably from 3 to 7 and more preferably from 3.5 to 6. The pH of a medium can be controlled with a base such as calcium hydroxide, sodium hydroxide, calcium carbonate and ammonia or an acid such as a sulfuric acid and hydrochloric acid.

A preferable example of the medium includes a liquid medium containing from 7.5 to 30% of carbon source, from 0.001 to 0.2% of ammonium sulfate, from 0.001 to 0.6% of potassium dihydrogen phosphate, from 0.01 to 0.1% magnesium sulfate heptahydrate, from 0.005 to 0.05% of zinc sulfate heptahydrate and from 3.75 to 20% calcium carbonate (concentrations are all expressed by % (w/v)).

To efficiently produce a C4 dicarboxylic acid using a transformed cell (a filamentous fungus as a host), production may be carried out in the steps mentioned below. More specifically, a C4 dicarboxylic acid can be efficiently produced by preparing a spore suspension of a transformed cell (step A), culturing the suspension in a culture solution to germinate the spore, thereby preparing a mycelium (step B1), preferably further proliferating the mycelium (step B2), and then culturing the mycelium prepared to produce the C4 dicarboxylic acid (step C). Note that, the culture step of a transformed cell in the present invention is not limited to the following steps.

<Step A: Preparation of Spore Suspension>

Spores of a filamentous fungus transformed are inoculated, for example, on a medium such as an inorganic agar medium (composition example: 2% glucose, 0.1% ammonium sulfate, 0.06% potassium dihydrogen phosphate, 0.025% magnesium sulfate heptahydrate, 0.009% zinc sulfate heptahydrate and 1.5% agar (concentrations are all expressed by % (w/v))) and PDA medium, and subjected to stationary culture at from 10 to 40° C., preferably from 27 to 30° C. for 7 to 10 days to form spores, which are then suspended in e.g., physiological saline to prepare a spore suspension. The spore suspension may or may not contain a mycelium.

<Step B1: Preparation of Mycelium>

The spore suspension obtained in step A is inoculated in a culture solution and cultured to germinate spores, thereby obtaining mycelia. The number of spores of a filamentous fungus to be inoculated in the culture solution is from $1 \times 10^2$ to $1 \times 10^8$ spores/mL (culture solution), preferably from $1 \times 10^2$ to $5 \times 10^4$ spores/mL (culture solution), more preferably from $5 \times 10^2$ to $1 \times 10^4$ spores/mL (culture solution) and further preferably from $1 \times 10^3$ to $1 \times 10^4$ spores/mL (culture solution). As the culture solution, a commercially available medium such as PDB medium, LB medium, NB medium, SB medium and SD medium, can be used. In view of germination rate and mycelium growth, a carbon source including a monosaccharide such as glucose and xylose, an oligosaccharide such as sucrose, lactose and maltose, or a polysaccharide such as starch; a biological component such as glycerin and citric acid; a nitrogen source such as ammonium sulfate, urea and amino acid; and other inorganic substances such as various salts including a sodium salt, a potassium salt, a magnesium salt, a zinc salt, an iron salt and a phosphate may be appropriately added to the culture solution. The preferable concentrations of a monosaccharide, oligosaccharide, polysaccharide and glycerin are from 0.1 to 30% (w/v); the preferable concentration of citric acid is from 0.01 to 10% (w/v); the preferable concentrations of ammonium sulfate, urea and amino acid are from 0.01 to 1% (w/v); and the preferable concentration of an inorganic substance is from 0.0001 to 0.5% (w/v). To the culture solution, the spore suspension is inoculated. The culture solution is cultured for preferably from 24 to 120 hours and more preferably from 48 to 72 hours, while stirring at preferably from 80 to 250 rpm and more preferably from 100 to 170 rpm and controlling a culture temperature to be from 25 to 42.5° C. The amount of the culture solution to be subjected to culture, which may be appropriately controlled depending upon the size of the culture vessel; may be, about from 50 to 100 mL, in the case of e.g., a 200 mL flask with a baffle, and about from 100 to 300 mL in the case of a 500 mL flask with a baffle. Owing to the culture, the spores inoculated are germinated and grow into mycelia.

<Step B2: Growth of Mycelium>

In view of improvement of C4 dicarboxylic acid productivity, it is preferable to perform a step (step B2) of proliferating the mycelium obtained in step B1 by further culture. The culture solution for proliferation to be used in step B2 is not particularly limited and may be sufficient if it is an inorganic culture solution routinely used and containing glucose; for example, a culture solution containing from 7.5 to 30% of glucose, from 0.05 to 0.2% of ammonium sulfate, from 0.03 to 0.6% of potassium dihydrogen phosphate, from 0.01 to 0.1% of magnesium sulfate heptahydrate, from 0.005 to 0.05% of zinc sulfate heptahydrate and from 3.75 to 20% of calcium carbonate (concentrations are all expressed by % (w/v)), may be mentioned. The amount of culture solution may be appropriately controlled depending upon the size of a culture vessel. For example, in the case of a 500 mL Erlenmeyer flask, the amount of culture solution may be sufficient if it is from 50 to 300 mL and preferably from 100 to 200 mL. To the culture solution, a mycelia cultured in step B1 was inoculated so as to obtain a rate of, as wet weight, from 1 to 6 g of mycelia/100 mL (culture solution) and preferably from 3 to 4 g of mycelia/100 mL (culture solution), and cultured for from 12 to 120 hours and preferably from 24 to 72 hours while stirring at from 100 to 300 rpm and preferably from 170 to 230 rpm and controlling a culture temperature to be from 25 to 42.5° C.

<Step C: Production of a C4 Dicarboxylic Acid>

The mycelium of a filamentous fungus obtained in the aforementioned procedure (step B1 or B2) is cultured to allow the fungus to produce a C4 dicarboxylic acid. The conditions of the culture may follow the culture conditions mentioned above and routinely used for filamentous fungi. The amount of medium can be about from 20 to 80 mL in the case of a 200 mL Erlenmeyer flask, about from 50 to 200 mL in the case of a 500 mL Erlenmeyer flask and about from 10 L to 15 L in the case of a 30 L jar fermenter; however, the amount of medium may be appropriately controlled depending upon the size of the culture vessel. The inoculation amount of the mycelium obtained in step B1 or B2 to the medium can be preferably, as wet weight, from 5 g to 90 g of mycelia/100 mL (medium) and more preferably from 5 g to 50 g of mycelia/100 mL (medium). Culture is preferably performed at a temperature of from 25 to 45° C. for 2 hours to 240 hours and preferably from 12 hours to 120 hours while stirring at from 100 to 300 rpm and preferably from 150 to 230 rpm. If a jar fermenter is used, aeration is preferably performed at from 0.05 to 2 vvm and more preferably from 0.1 to 1.5 vvm.

The transformed cell of the present invention is cultured in the above procedure to produce a C4 dicarboxylic acid. After cultivation, the C4 dicarboxylic acid is recovered from the cultured broth. If necessary, the C4 dicarboxylic acid recovered may be further purified. A method for recovering or purifying a C4 dicarboxylic acid from the cultured broth is not particularly limited and may be performed in accordance with a recovery or purification method known in the art. For example, the C4 dicarboxylic acid in the culture can be recovered or purified by removing cells and the like from a cultured broth by a method such as a gradient method, filtration and centrifugation, if necessary concentrating the remaining culture, and subjecting the concentrate to a method such as a crystallization method, an ion exchange method and a solvent extraction method or a combination of these.

The transformed cell of the present invention separated from the culture can be reused in producing a C4 dicarboxylic acid. For example, to the transformed cell of the present invention separated from the culture, the medium as mentioned above is newly added. The mixture is cultured again in the aforementioned conditions to produce a C4 dicarboxylic acid. Then the C4 dicarboxylic acid produced can be recovered from the medium. This process can be further repeated. In the production method of the present invention, cultivation of a transformed cell and recovery of a C4 dicarboxylic acid can be performed either one of a batch, semi-batch and continuous process.

4. Illustrative Embodiments

As an illustrative embodiment of the present invention, the following substances, production method, use and method will be further disclosed herein. However, the present invention is not limited to these embodiments.

[1] A transformed cell comprising an exogenous polynucleotide encoding a polypeptide consisting of an amino acid sequence represented by SEQ ID NO: 2, an amino acid sequence represented by SEQ ID NO: 22 or an amino acid sequence having an identity of at least 80% with any of the sequences.

[2] A transformed cell obtained by modifying a host cell containing a polynucleotide encoding a polypeptide consisting of an amino acid sequence represented by SEQ ID NO: 2, an amino acid sequence represented by SEQ ID NO: 22 or an amino acid sequence having an identity of at least 80% with any of the sequences, as a gene on a genome thereof, such that the regulatory region of the gene is modified so as to improve the transcript amount of the gene.

[3] Preferably, the transformed cell according to [1] or [2], in which the amino acid sequence having an identity of at least 80% with the amino acid sequence represented by SEQ ID No: 2 is an amino acid sequence having an identity of 80% or more, preferably 85% or more, more preferably 90% or more, further preferably 95% or more, still further preferably 96% or more, further more preferably 97% or more, further more preferably 98% or more, and furthermore preferably 99% or more with the amino acid sequence represented by SEQ ID No: 2; or an amino acid sequence having deletion, substitution, addition or insertion 1 or more and 10 or less, preferably 1 or more and 8 or less, more preferably 1 or more and 5 or less, and further preferably 1 or more and 3 or less amino acid(s), in the amino acid sequence represented by SEQ ID No: 2.

[4] The transformed cell according to any one of [1] to [3], in which the polypeptide consisting of an amino acid sequence represented by SEQ ID NO: 2 or an amino acid sequence having an identity of at least 80% with any of the sequences is preferably a multiple transmembrane polypeptide having 14 transmembrane helix structures, and more preferably, a multiple transmembrane polypeptide having a transmembrane helix structure in each of the corresponding regions to 53rd to 75th, 90th to 112th, 119th to 141st, 145th to 167th, 180th to 198th, 208th to 230th, 243rd to 265th, 275th to 294th, 315th to 337th, 347th to 369th, 376th to 398th, 408th to 430th, 443rd to 465th and 511th to 533rd amino acid regions of the amino acid sequence represented by SEQ ID NO: 2.

[5] The transformed cell according to [1] or [2], in which preferably, the amino acid sequence having an identity of at least 80% with the amino acid sequence represented by SEQ ID NO: 22 is an amino acid sequence having an identity of 80% or more, preferably 85% or more, more preferably 90% or more, further preferably 95% or more, still further preferably 96% or more, further more preferably 97% or more, further more preferably 98% or more, and further more preferably 99% or more with the amino acid sequence represented by SEQ ID NO: 22; or an amino acid sequence having deletion, substitution, addition or insertion of 1 or more and 10 or less, preferably 1 or more and 8 or less, more preferably 1 or more and 5 or less and further preferably 1 or more and 3 or less amino acid(s) with respect to the amino acid sequence represented by SEQ ID NO: 22.

[6] The transformed cell according to any one of [1], [2] and [5], in which the polypeptide consisting of an amino acid sequence represented by SEQ ID NO: 22 or an amino acid sequence having an identity of at least 80% with any of the sequences is preferably a multiple transmembrane polypeptide having 8 transmembrane helix structures and more preferably a multiple transmembrane polypeptide having a transmembrane helix structure in each of the corresponding regions to the 13th to 32nd, 42nd to 64th, 71st to 93rd, 97th to 119th, 131st to 153rd, 163rd to 182nd, 189th to 206th and 212th to 234th amino acid region in the amino acid sequence represented by SEQ ID NO: 22.

[7] The transformed cell according to any one of [1] to [4], in which preferably, the polynucleotide is a polynucleotide consisting of a nucleotide sequence represented by SEQ ID NO: 1 or a nucleotide sequence having an identity of at least 80% with any of the sequences.

[8] Preferably, the transformed cell according to [7], in which the nucleotide sequence having an identity of at least 80% with the nucleotide sequence represented by SEQ ID No: 1, is a nucleotide sequence having an identity of 80% or more, preferably 85% or more, more preferably 90% or more, further preferably 95% or more, still further preferably 96% or more, further more preferably 97% or more, further more preferably 98% or more, and further more preferably 99% or more with the nucleotide sequence represented by SEQ ID No: 1; or a nucleotide sequence having deletion, substitution, addition or insertion of 1 or more and 30 or less, preferably 1 or more and 24 or less, more preferably 1 or more and 15 or less and further preferably 1 or more and 9 or less nucleotide(s), with respect to the nucleotide sequence represented by SEQ ID No: 1.

[9] The transformed cell according to any one of [1], [2], [5] and [6], in which preferably the polynucleotide is a polynucleotide consisting of a nucleotide sequence represented by SEQ ID NO: 21 or a nucleotide sequence having an identity of at least 80% with any of the sequences.

[10] The transformed cell according to [9], in which
preferably the nucleotide sequence having an identity of at least 80% with the nucleotide sequence represented by SEQ ID NO: 21 is
a nucleotide sequence having an identity of 80% or more, preferably 85% or more, more preferably 90% or more, further preferably 95% or more, still further preferably 96% or more, further more preferably 97% or more, further more preferably 98% or more, and further more preferably 99% or more with the nucleotide sequence represented by SEQ ID NO: 21; or
a nucleotide sequence having deletion, substitution, addition or insertion of 1 or more and 30 or less, preferably 1 or more and 24 or less, more preferably 1 or more and 15 or less and further preferably 1 or more and 9 or less nucleotide(s) with respect to the nucleotide sequence represented by SEQ ID NO: 21.

[11] The transformed cell according to any one of [1] and [3] to [10], preferably, comprising a vector containing the polynucleotide or the polynucleotide integrated in a genomic DNA thereof.

[12] The transformed cell according to [11], in which preferably, the vector further contains a regulatory region operably linked to the polynucleotide.

[13] The transformed cell according to [12], in which preferably, the polynucleotide is integrated in a genomic DNA, together with a regulatory region operably linked to the polynucleotide.

[14] The transformed cell according to any one of [1] to [13], in which preferably the cell is a cell of a microbe.

[15] The transformed cell according to [14], in which the microbe is preferably a filamentous fungus.

[16] The transformed cell according to [15], in which the above filamentous fungus is preferably *Rhizopus*.

[17] The transformed cell according to [16], in which *Rhizopus* is preferably *Rhizopus delemar* or *Rhizopus oryzae* and more preferably *Rhizopus delemar*.

[18] The transformed cell according to any one of [1] to [17], in which C4 dicarboxylic acid productivity is preferably improved.

[19] The transformed cell according to [18], in which the C4 dicarboxylic acid productivity is improved by preferably 10% or more, more preferably 15% or more, further preferably 20% or more.

[20] The transformed cell according to [18] or [19], in which the C4 dicarboxylic acid is preferably fumaric acid, malic acid or succinic acid.

[21] A method for producing a C4 dicarboxylic acid, comprising culturing the transformed cell according to any one of [1] to [20].

[22] The production method according to [21], further comprising recovering a C4 dicarboxylic acid from the above culture.

[23] The production method according to [21] or [22], in which the C4 dicarboxylic acid is fumaric acid, malic acid or succinic acid.

[24] A method for producing a transformed cell, comprising
introducing a polynucleotide encoding a polypeptide consisting of an amino acid sequence represented by SEQ ID NO: 2, an amino acid sequence represented by SEQ ID NO: 22 or an amino acid sequence having an identity of at least 80% with any of the sequences, or a vector containing the polynucleotide into a host cell.

[25] A method for producing a transformed cell, comprising
modifying a host cell containing a polynucleotide encoding a polypeptide consisting of an amino acid sequence represented by SEQ ID NO: 2, an amino acid sequence represented by SEQ ID NO: 22 or an amino acid sequence having an identity of at least 80% with any of the sequences as a gene on a genome thereof, such that the regulatory region of the gene is modified to improve the transcript amount of the gene.

[26] A method for improving C4 dicarboxylic acid productivity in a host cell, comprising introducing a polynucleotide encoding a polypeptide consisting of an amino acid sequence represented by SEQ ID NO: 2, an amino acid sequence represented by SEQ ID NO: 22 or an amino acid sequence having an identity of at least 80% with any of the sequences or a vector containing the polynucleotide, into a host cell.

[27] The method for improving C4 dicarboxylic acid productivity in a host cell, comprising modifying a host cell containing a polynucleotide encoding a polypeptide consisting of an amino acid sequence represented by SEQ ID NO: 2, an amino acid sequence represented by SEQ ID NO: 22 or an amino acid sequence having an identity of at least 80% with any of the sequences as a gene on a genome thereof, more specifically, such that the regulatory region of the gene is modified so as to improve the transcript amount of the gene.

[28] The method according to [26] or [27], in which the C4 dicarboxylic acid productivity in a host cell is improved by preferably 10% or more, more preferably 15% or more, further preferably 20% or more.

[29] The method according to any one of [26] to [28], in which the C4 dicarboxylic acid is preferably fumaric acid, malic acid or succinic acid.

[30] The method according to any one of [24] to [29], in which
preferably, the amino acid sequence having an identity of at least 80% with the amino acid sequence represented by SEQ ID NO: 2 is
an amino acid sequence having an identity of 80% or more, preferably 85% or more, more preferably 90% or more, further preferably 95% or more, still further preferably 96% or more, further more preferably 97% or more, further more preferably 98% or more, and further more preferably 99% or more with the amino acid sequence represented by SEQ ID NO: 2; or
an amino acid sequence having deletion, substitution, addition or insertion of 1 or more and 10 or less, preferably 1 or more and 8 or less, more preferably 1 or more and 5 or less and further preferably 1 or more and 3 or less amino acid(s) with respect to the amino acid sequence represented by SEQ ID NO: 2.

[31] The method according to any one of [24] to [30], in which the polypeptide consisting of an amino acid sequence represented by SEQ ID NO: 2 or an amino acid sequence having an identity of at least 80% with any of the sequences is
preferably a multiple transmembrane polypeptide having 14 transmembrane helix structures and
more preferably, a multiple transmembrane polypeptide having a transmembrane helix structure in each of the corresponding regions to the 53rd to 75th, 90th to 112th, 119th to 141st, 145th to 167th, 180th to 198th, 208th to 230th, 243rd to 265th, 275th to 294th, 315th to 337th, 347th to 369th, 376th to 398th, 408th to 430th, 443rd to 465th and 511th to 533rd amino acid regions of the amino acid sequence represented by SEQ ID NO: 2.

[32] The method according to any one of [24] to [29], in which preferably, the amino acid sequence having an identity of at least 80% with an amino acid sequence represented by SEQ ID NO: 22 is an amino Acid sequence having an identity of 80% or more, preferably 85% or more, more preferably 90% or more, further preferably 95% or more, still further preferably 96% or more, further more preferably 97% or more, further more preferably 98% or more, and further more preferably 99.% or more with the amino acid sequence represented by SEQ ID NO: 22; or an amino acid sequence having deletion, substitution, addition or insertion of 1 or more and 10 or less, preferably 1 or more and 8 or less, more preferably 1 or more and 5 or less and further preferably 1 or more and 3 or less amino acid(s) with respect to the amino acid sequence represented by SEQ ID NO: 22.

[33] The method according to any one of [24] to [29] and [32], in which the polypeptide consisting of an amino acid sequence represented by SEQ ID NO: 22 or an amino acid sequence having an identity of at least 80% with any of the sequences is preferably a multiple transmembrane polypeptide having 8 transmembrane helix structures and more preferably, a multiple transmembrane polypeptide having a transmembrane helix structure in each of the corresponding regions to the 13th to 32nd, 42nd to 64th, 71st to 93rd, 97th to 119th, 131st to 153rd, 163rd to 182nd, 189th to 206th and 212th to 234th amino acid regions of the amino acid sequence represented by SEQ ID NO: 22.

[34] The method according to any one of [24] to [31], in which preferably, the polynucleotide is a polynucleotide consisting of a nucleotide sequence represented by SEQ ID NO: 1 or a nucleotide sequence having an identity of at least 80% with any of the sequences.

[35] The method according to [34], in which preferably, the nucleotide sequence having an identity of at least 80% with the nucleotide sequence represented by SEQ ID NO: 1 is a nucleotide sequence having an identity of 80% or more, preferably 85% or more, more preferably 90% or more, further preferably 95% or more, still further preferably 96% or more, further more preferably 97% or more, further more preferably 98% or more, and further more preferably 99% or more with the nucleotide sequence represented by SEQ ID NO: 1; or a nucleotide sequence having deletion, substitution, addition or insertion of 1 or more and 30 or less, preferably 1 or more and 24 or less, more preferably 1 or more and 15 or less and further preferably 1 or more and 9 or less nucleotide(s) with respect to the nucleotide sequence represented by SEQ ID NO: 1.

[36] The method according to any one of [24] to [29], [32] and [33], in which preferably, the polynucleotide is a polynucleotide consisting of a nucleotide sequence represented by SEQ ID NO: 21 or a nucleotide sequence having an identity of at least 80% with any of the sequences.

[37] The method according to [36], in which preferably, the nucleotide sequence having an identity of at least 80% with the nucleotide sequence represented by SEQ ID NO: 21 is a nucleotide sequence having an identity of 80% or more, preferably 85% or more, more preferably 90% or more, further preferably 95% or more, still further preferably 96% or more, further more preferably 97% or more, further more preferably 98% or more, and further more preferably 99% or more with the nucleotide sequence represented by SEQ ID NO: 21; or a nucleotide sequence having deletion, substitution, addition or insertion of 1 or more and 30 or less, preferably 1 or more and 24 or less, more preferably 1 or more and 15 or less and further preferably 1 or more and 9 or less nucleotide(s) with respect to the nucleotide sequence represented by SEQ ID NO: 21.

[38] The method according to any one of [24] to (37), in which the host cell is preferably a cell of a microbe.

[39] The method according to [38], in which the microbe is preferably a filamentous fungus.

[40] The method according to [39], in which the filamentous fungus is preferably *Rhizopus*.

[41] The method according to [40], in which *Rhizopus* is preferably *Rhizopus delemar* or *Rhizopus oryzae* and more preferably *Rhizopus delemar*.

EXAMPLES

The present invention will be more specifically described below based on Examples; however, the present invention is not limited to these.

Example 1 Production of Transformed Cell (1) Genome Extraction

To PDA medium, spores of *Rhizopus delemar* JCM (Japan Collection of Microorganisms/Riken) 5557 strain (hereinafter referred to as 5557 strain) were inoculated and cultured at 30° C. for 5 days. After completion of the cultivation, mycelia were placed together with metal cones for a 3 mL tube (Yasui Kikai Corporation) in a 3 mL disruption tube and immediately frozen in liquid nitrogen for 10 minutes or more. Thereafter, the mycelia were disrupted using a multi bead shocker (Yasui Kikai Corporation) at 1,700 rpm for 10 seconds. After completion of the disruption, 400 j.i.L of TE Buffer (pH8.0) (Nippon Gene Co., Ltd.) was added to the container and mixed by turning the container upside down, and then, 250 µL of an aliquot was taken and transferred to a 1.5 mL tube. From the mycelium solution, a genome was extracted using "Dr. GenTLE (for yeast)" (Takara Bio Inc.) in accordance with the protocol. To 50 µL of the resultant genome solution, 1 µL of RNaseA (Roche) was added and allowed to react at 37° C. for one hour. After completion of the reaction, an equivalent amount of phenol chloroform was added and mixed by tapping. The mixture was centrifuged at 4° C. and 14,500 rpm for 5 minutes. The supernatant was transferred to a new 1.5 mL tube. The treatment with phenol chloroform was repeated and then precipitation with ethanol was performed to obtain a solution of purified genome of 5557 strain.

(2) Preparation of cDNA (i) Extraction of Total RNA 6 g, in wet weight, of mycelia of 5557 strain was inoculated in 40 mL of liquid medium (1 g/L $(NH_4)_2SO_4$, 0.6 g/L $KH_2PO_4$, 0.25 g/L $MgSO_4 \cdot 7H_2O$, 0.09 g/L $ZnSO_4 \cdot 7H_2O$, 50 g/L calcium carbonate, 100 g/L glucose) and cultured at 35° C. and 170 rpm for 8 hours. Mycelia were recovered from the culture solution by filtration and washed twice with 100 mL of 0.85% physiological saline. After completion of the washing, extra water was removed by suction filtration. The mycelia (0.3 g) were weighed out, placed in a 3 mL crushing tube together with metal cones for a 3 mL tube (Yasui Kikai Corporation) and immediately placed in liquid nitrogen to freeze. The frozen mycelia thus obtained were crushed by a multi bead shocker (Yasui Kikai Corporation) at 1,700 rpm for 10 seconds. To the mycelia crushed, 500 μL of RLT buffer was added and mixed by turning the tube upside down, and then, 450 μL of an aliquot was subjected to RNeasy Plant Mini Kit (Qiagen) to extract total RNA. To 40 μL of the RNA solution thus obtained, 1 μL of DNaseI (TaKaRa) and 5 μL of 10×DNaseI buffer (USB Corporation) were added The reaction solution was filled up to 50 μL with RNase free water and allowed to react at 37° C. for 30 minutes or more to remove residual DNA in the solution. DNaseI (1 μL) was further add to the solution, which was allowed to react at 37° C. for 30 minutes and then subjected to phenol/chloroform extraction, followed by ethanol precipitation. The precipitate was dissolved in 50 μL of sterilized water. The concentration and purity of the RNA solution were measured by Qubit (Life Technologies). The RNA solution was appropriately diluted and the RNA extracted was assayed by Agilent 2100 Bioanalyzer (Agilent) and RNA6000 Pico Kit (Agilent). The resultant RNA solution, which was confirmed to have an RNA decomposition index: "RNA Integrity Number (RIN value)" of 6.0 or more, was used as total RNA.

(ii) Synthesis of cDNA cDNA was synthesized using SuperScriptIII First-Strand Synthesis SuperMix for qRT-PCR (Invitrogen). More specifically, 1 μg of the RNA solution obtained in (i) was filled up to 8 μL with DEPC water. To the RNA solution, 10 μL of 2×RT Reaxtion Mix, 2 μL of RT Enzyme Mix were added. The mixture was gently mixed and allowed to react at 25° C. for 10 minutes, 50° C. for 30 minutes and 85° C. for 5 minutes. After completion of the reaction, 1 μL of RNaseH was added to the solution and the mixture solution was allowed to react at 37° C. for 20 minutes and used as a cDNA solution.

(3) Preparation of Plasmid Vector (i) Introduction of trpC Gene Region in pUC18

Using the genomic DNA of 5557 strain obtained in (1) in the above, as a template, a DNA fragment containing a trpC gene (SEQ ID No: 3) was synthesized by PCR using primers oJK162 (SEQ ID No: 4) and oJK163 (SEQ ID No: 5). Subsequently, using plasmid pUC18 as a template, a DNA fragment was amplified by PCR using primers oJK164 (SEQ ID No: 6) and oJK165 (SEQ ID No: 7). The two fragments obtained above were ligated by In-Fusion HD Cloning Kit (Clontech) to construct plasmid pUC18-trpC.

(ii) Cloning of ADH1 Promoter and Terminator

Using the genomic DNA of 5557 strain obtained in (1) in the above, as a template, a DNA fragment containing a ADH1 promoter sequence (SEQ ID No: 8) and a DNA fragment containing a terminator sequence (SEQ ID No: 9) were amplified by PCR using a primer pair of oJK202 (SEQ ID No: 10) and oJK204 (SEQ ID No: 11) and a primer pair of oJK205 (SEQ ID No: 12) and oJK216 (SEQ ID No: 13), respectively. Subsequently, using plasmid pUC18-trpC obtained in (i) as a template, a DNA fragment was amplified by PCR using primer oJK210 (SEQ ID No: 14) and oJK211 (SEQ ID No: 15). The three fragments obtained above were ligated in the same manner as (i) to construct plasmid pUC18-trpC-Padh-Tadh. The plasmid thus obtained has ADH1 promoter and terminator arranged downstream of the trpC gene region, in order. Further, a Not I restriction enzyme recognition sequence was arranged downstream of ADH1 terminator.

(iii) Preparation of Plasmid Vector

Using cDNA of 5557 strain obtained in (2) in the above, as a template, a DNA fragment containing a gene (hereinafter referred to as "rdt5") represented by SEQ ID No: 1 was amplified by PCR using primers oJK513 (SEQ ID No: 16) and oJK514 (SEQ ID No: 17). Subsequently, using plasmid pUC18-trpC-Padh-Tadh obtained in (ii), as a template, a DNA fragment was amplified by PCR using primers oJK204 (SEQ ID No: 11) and oJK269-4 (SEQ ID No: 18). The two fragments obtained above were ligated in the same procedure as in (1) to construct plasmid pUC18-trpC-Padh-rdt5-Tadh. The plasmid thus obtained has a rdt5 gene represented by SEQ ID No: 1 inserted between the ADH promoter and the terminator.

Then, using the cDNA of 5557 strain obtained in (2) in the above, as a template, a DNA fragment containing a gene (hereinafter referred to as "rdt6") represented by SEQ ID NO: 21 was amplified by PCR using primers oJK515(SEQ ID NO: 23) and oJK516(SEQ ID NO: 24). Subsequently, using plasmid pUC18-trpC-Padh-Tadh obtained in (ii), as a template, a DNA fragment was amplified by PCR using primers oJK204(SEQ ID NO: 11) and oJK269-4(SEQ ID NO: 18). The two fragments obtained above were ligated in the same procedure as in (1) to construct plasmid pUC18-trpC-Padh-rdt6-Tadh. The resultant plasmid has rdt6 gene represented by SEQ ID NO: 1 inserted between the ADH promoter and the terminator.

The primers used in preparation of plasmid vector pUC18-trpC-Padh-rdt5-Tadh and pUC18-trpC-Padh-rdt6-Tadh are shown in Table 1.

TABLE 1

| Primer | Sequence (5'→3') | SEQ ID NO: |
| --- | --- | --- |
| oJK162 | cgagctcgaattatttaaatgaacagcaagttaataatctagaggg | 4 |
| oJK163 | tatgaccatgattacgatgagaggcaaaatgaagcgtac | 5 |
| oJK164 | atttaaataattcgagctcggtacccgggg | 6 |
| oJK165 | cgtaatcatggtcatagctg | 7 |
| oJK202 | tagagggaaaaagagagaattgaaatagg | 10 |
| oJK204 | ttttgttatttaattgtattaattgataatg | 11 |
| oJK205 | aattaaataacaaaatcattttaattacgcattttc | 12 |
| oJK216 | catgattacgcggccgcgccattataatgcactagtg | 13 |
| oJK210 | ctcttttttccctctaatgagaggcaaaatgaagcgtac | 14 |
| oJK211 | aattaaataacaaaaatgtcttctatcgaaacctccaaaatctc | 15 |
| oJK513 | aattaaataacaaaaatggaaacgacgaattcatccaatacc | 16 |
| oJK514 | gcgtaattaaaatgactattctggagaggaggcatttactttac | 17 |
| oJK269-4 | tcattttaattacgcattttcatttactaatttgttacatttgataacg | 18 |
| oJK515 | aattaaataacaaaaatgggaaatttggactttaaaatcaaattg | 23 |
| oJK516 | gcgtaattaaaatgatcaagaaagcaaaggtgttctttcac | 24 |

(4) Introduction of Gene in Host Cell (i) Preparation of Tryptophan Auxotrophic Strain A tryptophan auxotrophic strain used as a host cell for gene introduction was selected from mutated strains which had been obtained by introducing a mutation to 5557 strain by ion beam irradiation. Ion beam irradiation was carried out at the ion irradiation facility of Takasaki Advanced Radiation Research Institute (TIARA: Takasaki Ion Accelerators for Advanced Radiation Application) of the Japan Atomic Energy Agency. Irradiation was carried out by accelerating $^{12}C^{5+}$ by using AVF cyclotron and applying 100 to 1.250 Gray at an energy of 220 MeV. Spores were recovered from the mycelia irradiated. From the spores, a tryptophan auxotrophic strain, *Rhizopus delemar* 02T6 strain (hereinafter, referred to as 02T6 strain) was obtained. 02T6 Strain has a deletion of a single base at 2093rd position of the trpC gene coding region (SEQ ID No: 3) (full length: 2.298 bp).

(ii) Amplification of Plasmid Vector

*Escherichia coli* DH5α strain (Nippon Gene Co., Ltd.) was transformed separately by plasmid vectors pUC18-trpC-Padh-Tadh, pUC18-trpC-Padh-rdt5-Tadh and pUC18-trpC-Padh-rdt6-Tadh prepared in (3) in the above using a competent cell transformation method. Each of the transformed cells obtained were allowed to stand still at 37° C. overnight. The resultant colonies were inoculated in 2 mL of LBamp liquid medium (Bacto Trypton 1%, Yeast Extract 0.5%, NaCl 1%, ampicillin sodium 50 μg/mL) and cultured at 37° C. overnight. From the cultured solution, each of the plasmid vectors was purified using a high pure plasmid isolation kit (Roche Life Science).

(iii) Introduction of Plasmid Vector in Host Cell

Each 10 μL of the DNA solutions (1 μg/μL) of plasmid vectors pUC18-trpC-Padh-Tadh, pUC18-trpC-Padh-rdt5-Tadh and pUC18-trpC-Padh-rdt6-Tadh obtained in (ii) was added to 100 μL of a gold particle solution (60 mg/mL). Thereafter, 40 μL of 0.1 M spermidine was added to the solution mixture and sufficiently stirred by a vortex. Further, 100 μL of 2.5M $CaCl_2$ was added to the solution mixture and stirred for one minute by a vortex, then centrifuged at 6,000 rpm for 30 seconds and the supernatant was removed. To the resultant precipitate, 200 μL of 70% EtOH was added. The solution was stirred for 30 seconds by a vortex and centrifuged at 6,000 rpm for 30 seconds and the supernatant was removed. The resultant precipitate was resuspended in 100 μL of 100% EtOH Subsequently, to the spores of 02T6 strain prepared in (i), a gene was introduced by GDS-80 (Nepa Gene Co., Ltd.) using the DNA-gold particle solution in the above. The spores having the gene introduced therein were subjected to stationary culture in an inorganic agar medium (20 g/L glucose, 1 g/L ammonium sulfate, 0.6 g/L potassium dihydrogen phosphate, 0.25 g/L magnesium sulfate heptahydrate, 0.09 g/L zinc sulfate heptahydrate, 15 g/L agar) at 30° C. for about a week. The mycelia grown were partly scraped off by a platinum loop and suspended in TE (pH8.0) (Nippon Gene Co., Ltd.). The suspension solution was treated at 95° C. for 15 minutes to extract a nucleic acid from transformed strains. A PCR reaction was carried out using the nucleic acid as a template and primers oJK438 (SEQ ID No: 19) and oJK439 (SEQ ID No: 20). The strain, which was confirmed to have a desired DNA fragment introduced therein, was selected as a transformed strain. The PCR primers are shown in Table 2. A strain in which pUC18-trpC-Padh-rdt5-Tadh containing DNA (where rdt5 gene is ligated downstream of ADH1 promoter) was introduced was designated as RDT5 strain; and a strain in which pUC18-trpC-Padh-rdt6-Tadh containing DNA (where rdt6 gene is ligated downstream of ADH1 promoter) was introduced was obtained as RDT6 strain. In contrast, a strain in which plasmid vector pUC18-trpC-Padh-Tadh containing DNA (where rdt5 gene or rdt6 gene is not inserted) was introduced was obtained as a negative control strain (hereinafter referred to as NC strain). The remaining mycelia were scraped off by a platinum loop and vigorously mixed in a spore recovery solution (8.5 g/L sodium chloride, 0.5 g/L polyoxyethylene sorbitan monooleate). After mixing, the spore suspension was filtered through a 3GP100 glass filter (cylindrical funnel) (SIBATA SCIENTIFIC TECHNOLOGY LTD.). The filtrate was used as a spore solution. The number of spores in the spore solution was measured by a hemocytometer (counting chamber, D=1/50 mm·1/400 $mm^2$).

TABLE 2

| Primer | Sequence (5'→3') | SEQ ID NO: |
|---|---|---|
| oJK438 | gttccttgatgtggatttgtg | 19 |
| oJK439 | gggtgtatctctgtcctattcatg | 20 |

Example 2 C4 Dicarboxylic Acid Productivity of RDT5 Strain and RDT6 Strain (1) Cultivation of Transformed Strain (i) Preparation of Mycelium A 500 mL Erlenmeyer flask with a baffle (Asahi Glass Co., Ltd.) was charged with 200 mL of SD/-Trp medium (Clontech) containing sorbitan monolaurate (Leodol SP-L10 (Kao Corp.)) in a final concentration of 0.5% (v/v). Each of the spore solutions of RDT5 strain, RDT6 strain and NC strain prepared in Example 1 was inoculated at a rate of $1 \times 10^3$ spores/mL (medium) and then cultured at 27° C. for 3 days while stirring at 170 rpm. The resultant cultured broth was filtered through a stainless sieve (mesh size: 250 μm (AS ONE Corporation)) previously sterilized to recover mycelia on the filter.

(ii) Proliferation of Mycelium

To 100 mL of the inorganic culture solution (1 g/L $(NH_4)_2SO_4$, 0.6 g/L $KH_2PO_4$, 0.25 g/L $MgSO_4.7H_2O$, 0.09 g/L $ZnSO_4.7H_2O$, 50 g/L calcium carbonate, 100 g/L glucose) placed in a 500 mL Erlenmeyer flask, 5.0 to 8.0 g of the wet mycelia recovered in (i) was inoculated and cultured at 27° C. for about 40 hours, while stirring at 220 rpm. The resultant cultured broth was filtered by using a stainless screen filter holder (Millipore) previously sterilized to recover mycelia on the filter. The mycelia were further washed with 200 mL of physiological saline on the filter holder. The physiological saline used for washing was removed by suction filtration.

(2) Evaluation of C4 Dicarboxylic Acid Productivity of Transformed Strain

Each wet mycelia (6.0 g) of RDT5 strain, RDT6 strain and NC strain obtained in (1) in the above was inoculated in 40 mL of an inorganic culture solution for productivity evaluation (0.175 g/L $(NH_4)_2SO_4$, 0.06 g/L $KH_2PO_4$, 0.375 g/L $MgSO_4.7H_2O$, 0.135 g/L $ZnSO_4.7H_2O$, 50 g/L calcium carbonate, 100 g/L glucose) placed in a 200 mL Erlenmeyer flask and cultured at 35° C. while stirring at 170 rpm. After cultivation for 56 hours, the culture supernatant containing no mycelia was recovered. Fumaric acid, malic acid, succinic acid and glucose were quantified in accordance with the procedure described later in Reference Example 1 and conversion rates (yield) of C4 dicarboxylic acids from glucose were calculated. Based on the obtained conversion rates in RDT5 strain, RDT6 strain and NC strain, the productivity improvement rates of individual C4 dicarboxylic acids in RDT5 strain and RDT6 strain were calculated in accordance with the following expression.

Improvement rate (%)=(conversion rate in RDT5 strain or RDT6 strain/conversion rate in NC strain)×100−100

The results are shown in Table 3. In RDT5 strain, productivity of malic acid was improved by 73.6%, fumaric acid by 24.3% and succinic acid by 32.1%, compared to the respective productivity in NC strain having no rdt5 gene or rdt6 gene introduced therein. In RDT6 strain, productivity of malic acid was improved by 49.5%, fumaric acid by 21.1% and succinic acid by 28.6%, compared to the respective productivity in NC strain.

TABLE 3

| | Conversion rate from glucose (%) | | |
|---|---|---|---|
| Name of strain | Malic acid | Fumaric acid conversion rate | Succinic acid conversion rate |
| RDT5 strain | 4.2 | 28.3 | 1.5 |
| RDT6 strain | 3.6 | 27.6 | 1.4 |
| NC strain | 2.4 | 22.8 | 1.1 |

| | Productivity improvement rate (%) | | |
|---|---|---|---|
| Name of strain | Malic acid | Fumaric acid | Succinic acid |
| RDT5 strain | 73.6 | 24.3 | 32.1 |
| RDT6 strain | 49.5 | 21.1 | 28.6 |

Reference Example 1 Quantification of C4 Dicarboxylic Acid and Glucose

C4 dicarboxylic acids (fumaric acid, malic acid and succinic acid) and glucose in a culture supernatant were quantified by HPLC.

The culture supernatant to be subjected to HPLC analysis was appropriately diluted in advance with 37 mM sulfuric acid. Insoluble matter was removed by DISMIC-13cp (0.20 μm cellulose acetate membrane, ADVANTEC) or AcroPrep 96 filter plate (0.2 μm GHP membrane, Pall Corporation).

As the HPLC apparatus, LaChrom Elite (Hitachi High-Technologies Corporation) was used. As the analysis column, a polymer column for organic acid analysis, ICSep ICE-ION-300 (7.8 mm I.D.×30 cm, TRANSGENOMIC) to which ICSep ICE-ION-300 Guard Column Cartridge (4.0 mm I.D.×2.0 cm, TRANSGENOMIC) was connected, was used. As the eluent, 10 mM sulfuric acid was used. Elution was carried out at a flow rate of 0.5 mL/minute and at a column temperature of 50° C. Each of C4 dicarboxylic acids and glucose were detected using a UV detector (detection wavelength 210 nm) and a differential refractive index detector (RI detector). Concentration calibration curves were prepared by using standard samples [fumaric acid (distributor code 063-00655, Wako Pure Chemical Industries, Ltd.), malic acid (distributor code 135-00562, Wako Pure Chemical Industries, Ltd.), succinic acid (distributor code 194-04335, Wako Pure Chemical Industries, Ltd.) and glucose (distributor code 045-31162, Wako Pure Chemical Industries, Ltd.)]. Individual components were quantified based on respective concentration calibration curves.

The value obtained by subtracting the amount of glucose quantified in the medium from the initial amount of glucose in the medium is regarded as the amount of glucose consumed. The ratios (%) of individual C4 dicarboxylic acid amounts relative to the amount of glucose consumed were calculated and regarded as conversion rates (yield) of individual C4 dicarboxylic acids.

The invention claimed is:

1. A method for producing a C4 dicarboxylic acid, comprising
  (1) culturing a transformed cell,
  wherein the cell is a yeast or filamentous fungus cell,
  wherein the cell is transformed with a polynucleotide that encodes a polypeptide;
  wherein the sequence of the polypeptide consists of the amino acid sequence of SEQ ID NO: 2, the amino acid sequence of SEQ ID NO: 22, or an amino acid sequence having a sequence identity of at least 90% with SEQ ID NO:2 or SEQ ID NO:22;
  (2) expressing the polypeptide; and
  (3) producing C4 dicarboxylic acid,
  wherein, as a result of the expressing, C4 dicarboxylic acid productivity is improved in the transformed cell as compared to that obtained using a cell that is the same except that it has not been transformed with the polynucleotide.

2. The method of claim 1, wherein the polynucleotide comprises the nucleotide sequence of SEQ ID NO:1, the nucleotide sequence of SEQ ID NO: 21 or a nucleotide sequence that has a sequence identity of at least 90% with SEQ ID NO:1 or SEQ ID NO:21.

3. The method according to claim 1, wherein the transformed cell comprises a vector that comprises the polynucleotide.

4. The method according to claim 1, wherein the transformed cell is a cell of a filamentous fungus.

5. The method of claim 4, wherein the filamentous fungus is *Rhizopus*.

6. The method of claim 5, wherein the filamentous fungus is *Rhizopus delemar*.

7. The method of claim 1, further comprising recovering the C4 dicarboxylic acid from broth in which the transformed yeast or fungal cell was cultured.

8. The method of claim 1, wherein the C4 dicarboxylic acid is fumaric acid, malic acid or succinic acid.

9. A method for improving C4 dicarboxylic acid productivity of a yeast or filamentous fungus cell, comprising
- (1) transforming the yeast or filamentous fungus cell with a polynucleotide that encodes a polypeptide, wherein the sequence of the polypeptide consists of the amino acid sequence of SEQ ID NO:2, the amino acid sequence of SEQ ID NO:22, or an amino acid sequence having a sequence identity of at least 90% with SEQ ID NO:2 or SEQ ID NO:22,
- (2) expressing the polypeptide, and
- (3) producing C4 dicarboxylic acid,
- wherein, as a result of the expressing, C4 dicarboxylic acid productivity is improved in the transformed cell as compared to that obtained using a cell that is the same except that it has not been transformed with the polynucleotide.

10. The method of claim 9, wherein the nucleotide sequence that encodes the polypeptide consists of the nucleotide sequence of SEQ ID NO: 1, the nucleotide sequence of SEQ ID NO: 21 or a nucleotide sequence having a sequence identity of at least 90% with SEQ ID NO:1 or SEQ ID NO:21.

11. The method of claim 9, wherein the cell is the cell of a filamentous fungus.

12. The method of claim 11, wherein the filamentous fungus is *Rhizopus*.

13. The method of claim 12, wherein *Rhizopus* is *Rhizopus delemar*.

14. A transformed yeast or filamentous fungus cell, wherein the cell is transformed with a polynucleotide that encodes a polypeptide, wherein the sequence of the polypeptide consists of the amino acid sequence of SEQ ID NO: 2, the amino acid sequence of SEQ ID No 22, or an amino acid sequence having a sequence identity of at least 90% with SEQ ID NO:2 or SEQ ID NO:22; and
- wherein expressing the polypeptide in the transformed cell improves C4 dicarboxylic acid productivity in the transformed cell as compared to that obtained using a cell that is the same except that it has not been transformed with the polynucleotide; and
- wherein the amount of mRNA that encodes the polypeptide is increased in the transfoiiiied cell as compared to that obtained using a cell that is the same except that it has not been transformed with the polynucleotide.

15. The transformed cell of claim 14, comprising a vector that comprises the polynucleotide.

* * * * *

UNITED STATES PATENT AND TRADEMARK OFFICE
CERTIFICATE OF CORRECTION

PATENT NO. : 10,787,686 B2
APPLICATION NO. : 15/767808
DATED : September 29, 2020
INVENTOR(S) : Jitsuro Kaneda Page 1 of 1

It is certified that error appears in the above-identified patent and that said Letters Patent is hereby corrected as shown below:

On the Title Page

Column 1, item (87), in "PCT Pub. Date," delete "Apr. 5, 2017" and insert -- May 4, 2017 --, therefor.

Signed and Sealed this
Fifteenth Day of December, 2020

Andrei Iancu
*Director of the United States Patent and Trademark Office*

SEQUENCE LISTING

```
<160> NUMBER OF SEQ ID NOS: 24

<210> SEQ ID NO 1
<211> LENGTH: 1776
<212> TYPE: DNA
<213> ORGANISM: Rhizopus delemar

<400> SEQUENCE: 1
atggaaacga cgaattcatc caataccaat atctctgatt caacagtgga tcaatcaata      60 tctcacaccgg cacctgtaac cgaaaaaacg gaaacagtaa acgaagataa aaaactatcc     120
actgtagaag aatacaagaa taagaaaact aatcgtttat taacttttat tggtcttcaa     180
gtagccctct ttttgtctgc tctcgacagt actattatat caacagcatt gcctagaatt     240
gggtctgatt tcaaccaaat gacaattgtt tcatgggttg ctacagctta catcttgacg     300
tttgatgcat tcaaccatt gtttgctaaa ttttctgata tttttggtcg taaatggatt     360
ctcatgtttg gcattggatt gttttatttt ggatccgtgt tatgtggtgc tgcaacaact     420
atgattatgc tgatcgttgc aagagccatt gctggtattg tgctgcagg tataaattct     480 atggttttta ttattatttc agatattgta ccattggaaa agagaggaag ttatcaaggc     540
ataattaatg ctgtgtttgc tttggcaagt gtctttggtc cattgatcgg tggttcattt     600
actgattatg ttacatggag atggaacttt tatatcaatc ttcctattgg tgccgtagct     660
gttgcagttc ttttatattt cctgagatta cctacaccta aatccaagct ttccgagaaa     720
```

```
ttaaagcgtg tggactacat aggtactgtg atcgtactgg ccttttctac cttgttctta      780 ttggcccta  actttggggg acaaacattc ccttggaagt cagctgctgt cattgtaccc      840
ttggttctct cagttctttt ggtaggcctg ctgatggttg tcgaaaaaaa atttgccaaa      900
gagcctttga tgccaccaag gctatttaga atcgatctg  tggtaagcgt cttgtttgtg      960
aattggttct ttggcatgtc cttctttct  gctgtttatt atcttccagt ctatttccag     1020
gttgtccgta acgatagtgc catgtggtcc ggtattcgtt taattcccat gcaacttgtg     1080
ctttgtttta tttctacttt ggcaggtctt actatatcaa agacaggtgt tacagacca      1140 atgatttgta ttggtatggg tctaatgaca ctgtggattg gactcactac tttatatgat     1200
caaacaatac cattttccca gattatggt  atcactattc ttggctctgg atcacttgga     1260
tgtctctttt catctactat tatcgctctt caagcctctg tggaaataaa agatattgct     1320
gttgtcactg gtctaggtaa ctttttctcgt atccttggtg gcgccttagg tgttgccata     1380
tcctctgctg ttttgaattc acatttaaat caagagcttc ctaatctttt acctattgat     1440
gaagctacta agtcattca  atcctcagaa tatgtcaacc acggtttacc agagcaatat     1500
aaggtgctag ctattgaagt ctatgttcat ggacttcaaa tgatttggta tgtcttgata     1560
gctatgtctg gattaggctt tattgcttcg ttctttgtca acatcattc  tgtacgtcgc     1620 catgtcaaag ctgctgcagc tgctaaacaa ggaaatgaag ccgataaagt tgatgacgta     1680
gttgttgaaa tagcttcttc aatagaagaa gaaattaaag atggctccgt attatcaaag     1740
actgagcgta agtaaatgc  ctcctctcca gaatag                                1776
```

<210> SEQ ID NO 2
<211> LENGTH: 591
<212> TYPE: PRT
<213> ORGANISM: Rhizopus delemar

<400> SEQUENCE: 2

```
Met Glu Thr Thr Asn Ser Ser Asn Thr Asn Ile Ser Asp Ser Thr Val
1               5                   10                  15

Asp Gln Ser Ile Ser Thr Pro Ala Pro Val Thr Glu Lys Thr Glu Thr
            20                  25                  30

Val Asn Glu Asp Lys Lys Leu Ser Thr Val Glu Glu Tyr Lys Asn Lys
        35                  40                  45

Lys Thr Asn Arg Leu Leu Thr Phe Ile Gly Leu Gln Val Ala Leu Phe
    50                  55                  60

Leu Ser Ala Leu Asp Ser Thr Ile Ile Ser Thr Ala Leu Pro Arg Ile
65                  70                  75                  80

Gly Ser Asp Phe Asn Gln Met Thr Ile Val Ser Trp Val Ala Thr Ala
                85                  90                  95

Tyr Ile Leu Thr Phe Asp Ala Phe Gln Pro Leu Phe Ala Lys Phe Ser
            100                 105                 110

Asp Ile Phe Gly Arg Lys Trp Ile Leu Met Phe Gly Ile Gly Leu Phe
        115                 120                 125

Leu Phe Gly Ser Val Leu Cys Gly Ala Ala Thr Thr Met Ile Met Leu
    130                 135                 140

Ile Val Ala Arg Ala Ile Ala Gly Ile Gly Ala Gly Ile Asn Ser
145                 150                 155                 160

Met Val Phe Ile Ile Ser Asp Ile Val Pro Leu Glu Lys Arg Gly
                165                 170                 175

Ser Tyr Gln Gly Ile Ile Asn Ala Val Phe Ala Leu Ala Ser Val Phe
```

```
            180                 185                 190
Gly Pro Leu Ile Gly Gly Ser Phe Thr Asp Tyr Val Thr Trp Arg Trp
            195                 200                 205

Asn Phe Tyr Ile Asn Leu Pro Ile Gly Ala Val Ala Val Ala Val Leu
210                 215                 220

Leu Tyr Phe Leu Arg Leu Pro Thr Pro Lys Ser Lys Leu Ser Glu Lys
225                 230                 235                 240

Leu Lys Arg Val Asp Tyr Ile Gly Thr Val Ile Val Leu Ala Phe Ser
                245                 250                 255

Thr Leu Phe Leu Leu Ala Leu Asn Phe Gly Gln Thr Phe Pro Trp
            260                 265                 270

Lys Ser Ala Ala Val Ile Val Pro Leu Val Leu Ser Val Leu Leu Val
            275                 280                 285

Gly Leu Leu Met Val Val Glu Lys Lys Phe Ala Lys Glu Pro Leu Met
            290                 295                 300

Pro Pro Arg Leu Phe Arg Asn Arg Ser Val Val Ser Val Leu Phe Val
305                 310                 315                 320

Asn Trp Phe Phe Gly Met Ser Phe Ser Ala Val Tyr Tyr Leu Pro
                325                 330                 335

Val Tyr Phe Gln Val Val Arg Asn Asp Ser Ala Met Trp Ser Gly Ile
                340                 345                 350

Arg Leu Ile Pro Met Gln Leu Val Leu Cys Phe Ile Ser Thr Leu Ala
            355                 360                 365

Gly Leu Thr Ile Ser Lys Thr Gly Val Tyr Arg Pro Met Ile Cys Ile
            370                 375                 380

Gly Met Gly Leu Met Thr Leu Trp Ile Gly Leu Thr Thr Leu Tyr Asp
385                 390                 395                 400

Gln Thr Ile Pro Phe Ser Gln Ile Tyr Gly Ile Thr Ile Leu Gly Ser
                405                 410                 415

Gly Ser Leu Gly Cys Leu Phe Ser Ser Thr Ile Ile Ala Leu Gln Ala
                420                 425                 430

Ser Val Glu Ile Lys Asp Ile Ala Val Val Thr Gly Leu Gly Asn Phe
            435                 440                 445

Ser Arg Ile Leu Gly Gly Ala Leu Gly Val Ala Ile Ser Ser Ala Val
450                 455                 460

Leu Asn Ser His Leu Asn Gln Glu Leu Pro Asn Leu Leu Pro Ile Asp
465                 470                 475                 480

Glu Ala Thr Lys Val Ile Gln Ser Ser Glu Tyr Val Asn His Gly Leu
                485                 490                 495

Pro Glu Gln Tyr Lys Val Leu Ala Ile Glu Val Tyr Val His Gly Leu
                500                 505                 510

Gln Met Ile Trp Tyr Val Leu Ile Ala Met Ser Gly Leu Gly Phe Ile
            515                 520                 525

Ala Ser Phe Phe Val Lys His His Ser Val Arg Arg His Val Lys Ala
530                 535                 540

Ala Ala Ala Lys Gln Gly Asn Glu Ala Asp Lys Val Asp Asp Val
545                 550                 555                 560

Val Val Glu Ile Ala Ser Ser Ile Glu Glu Ile Lys Asp Gly Ser
                565                 570                 575

Val Leu Ser Lys Thr Glu Arg Lys Val Asn Ala Ser Ser Pro Glu
                580                 585                 590

<210> SEQ ID NO 3
```

```
<211> LENGTH: 2298
<212> TYPE: DNA
<213> ORGANISM: Rhizopus delemar

<400> SEQUENCE: 3
atgaccactt tacttattga caactacgac agttttactt ataatgtcta tcaatacttg      60
agctgccaag gcgccaatgt agttgtctac agaaacgaca aaatcaccat ttccgaaatt     120
gagcaattgg ctcctcgcaa tattgtcatc tcacctggcc ctggccaccc ttccaccgat     180
gccggtgtct ctcgagaggc cattcgagct tttgcaggaa agattcccat cttgggtatt     240
tgtatgggtc agcaatgtat gtatgaagtg tacggtggta aagtgtcata tgcaggtgat     300
attgtgcatg gcaaggcatc cagcatcaag catgacagtc gaggtatctt caagggcgtt     360
cctcaaaaca acatggtcac tcgttaccat tcccttgctg gcatgccttc tactttacct     420
gaaacattag aagtcactgc gactaccgac gatggtatca tcatgggcat tcgacacaag     480
gaatacactg tcgaaggtgt tcagttccat cctgaaagta tcctttgtga cacggacat      540 acgatgatca acaacttctt aagcttgcgt ggtggcacct gggaagagaa tcctgcagcc     600
ggtgttgtct ttaagaaagc tcgttccgaa acacccaaaa tcagtgctag tgaatcccaa     660
ctcgatctct ctcagcaaca acctgccgca gcaccttcca tcttgacccg catttactct     720
caacgactca aggatgttca ggcagccaag gagattcccg ccagacatt tgaagattta      780 gaaaactttt aaagttgca cgtcgcccca cctcttcaag acgtcgtcgc tcgcgtgcgt      840
caaagcaagc ccgccttgat ggccgaagtc aagcgtgcct ctccctcgaa aggaaacatt     900
gatgtttcgg ccaacgcggc tgagcaggca cttcaatatg ctttagcagg tgcaagcgtc     960
gtctctgttc tgactgaacc caaatggttc cgcggtacga ttcatgatat gcatcaggtc    1020
cgagaggcct tgagccatct gcccaaccgt ccttgtgtgt tgagaaagga ttttattgtc    1080
gatcgctatc aaatcttgga aggttgtctg tacggtgctg atactatctt gttgatcgtg    1140
gccatgctga atgatgaaca actgcacgaa ttgtatcact atgcgaaatc attaggtatg    1200
gaacccttgg tcgaagtcaa taatacggaa gagatggccc gtgccaatgc tttgggcgca    1260
cgtctggtgg tgttaataa tcgcaacttg cacagctttg atgttgatat ggaaaccacg    1320
agtcgattgg tagagatggt gcctgaagga acgatcttgt gtgcacttc tggtattact     1380 ggacgagctg atgttgaaat gtacgtcaaa cagggtgtgc acgctgtctt ggtgggtgaa    1440
gccctgatgc gtgcttggaa tttgaaggag tttgtgtctg atttgttggg tcatgaaaag    1500
aaggatcctg tgcctgtgtc caaggaatca aaatcttcac tagtcaaggt atgtggtatc    1560
tctagtgtgg atgcagcagt tgaagcagcc aagtcagggg ctgacttgat tggtcttatc    1620
tttgctgaaa agtccaaacg aaaagtgtct ttggaaagag ctcaagaaat cgtgtcctca    1680
gtgcgtgcgt tggatattca agtcaaacga acgttatcaa atgatgattc tcaactggat    1740
tggttccaga tgcacaagcg tctcttggaa aagcgagcaa gaaaaccttt ggtagttggc    1800
gtgtttgtga atcaatcgat tgaatacatg actgaggtgg caacgacagt cggactggac    1860
cttattcagc tgcatggaac cgaatcaacg gagcttgcac gctatttacc cgtgcctgtc    1920
atcaaagctt tccatatcga cagtggtgag ttcaatgaag ctcagatacc aaacctaaat    1980
caaccaggct cttatcatta tgtcttactg gacgctaaag tgcccagctt accatcggat    2040
caacaaggtg gacgtggtgt caagtttgat tggtcaattg ctaccaaaat cgtgaaacat    2100
aggcactttg agttttggg taatcaagat ttccctgtca tcttggctgg tgggttggat    2160
cctaccaatg tggcatctgc cattcaacag gtgaaaccct ggattgtgga tgtgtcgagt    2220
```

```
ggtgttgaaa cagatggagt gaaggattta gaaaagattc gtgcctttgt taaaactgtc    2280
cagtcaacac aattttaa                                                 2298

<210> SEQ ID NO 4
<211> LENGTH: 46
<212> TYPE: DNA
<213> ORGANISM: Artificial
<220> FEATURE:
<223> OTHER INFORMATION: Synthetic oligonucleotide

<400> SEQUENCE: 4
cgagctcgaa ttatttaaat gaacagcaag ttaataatct agaggg                    46

<210> SEQ ID NO 5
<211> LENGTH: 39
<212> TYPE: DNA
<213> ORGANISM: Artificial
<220> FEATURE:
<223> OTHER INFORMATION: Synthetic oligonucleotide

<400> SEQUENCE: 5
tatgaccatg attacgatga gaggcaaaat gaagcgtac                            39

<210> SEQ ID NO 6
<211> LENGTH: 30
<212> TYPE: DNA
<213> ORGANISM: Artificial
<220> FEATURE:
<223> OTHER INFORMATION: Synthetic oligonucleotide

<400> SEQUENCE: 6
atttaaataa ttcgagctcg gtacccgggg                                      30

<210> SEQ ID NO 7
<211> LENGTH: 20
<212> TYPE: DNA
<213> ORGANISM: Artificial
<220> FEATURE:
<223> OTHER INFORMATION: Synthetic oligonucleotide

<400> SEQUENCE: 7
cgtaatcatg gtcatagctg                                                 20

<210> SEQ ID NO 8
<211> LENGTH: 1000
<212> TYPE: DNA
<213> ORGANISM: Rhizopus delemar

<400> SEQUENCE: 8
tagagggaaa aagagagaat tgaaatagga gaggatgagt caaaatatag tttacataaa     60
atttctcttt tttgtgttaa atataatcta atagcagggg ttttcttagt ttacgtttat    120
atcaaagtta tcaagcatac acttttttat gattttcat actttaatcc cttttagtat     180
tctattgttt gaaaggagag aaaaaacagc tgagggtacg gtgcacacga gatcttacga    240
taattttcct gcccaacagg aaagaagtaa ttgatcttga ttgacgctcg gagtttgcac    300
gttcggagtt tgcacttcac attgagttat actcttactt attttgaagg aagggacgag    360
aaaagatgta aatataataa taacagtagt aaatagtatg cgcatcaaga acagctacca    420
acaaaagaga gaaatatgag cttaataatg aacaatgtaa atggcagaat gaaatttaat    480
tatcaaagcg gcatctttca gaccttccgt tacttccgat agagttttttt atgcaaagta    540
```

| | | |
|---|---|---|
| ataacaactg tatatataaa aaaaagaagg ttatcaagca aaagccacaa tgtcatatct | 600 | |
| ggaataatca agagtaacta ttgaatgttg gtagccaaaa gaggcacgta attttatgac | 660 | |
| gaaatatcac acaaaaagat tattttgaca attcatgaat aggacagaga tacaccctaa | 720 | |
| acatgaaatg taagctatat ttaaacacct caagttaatt ttgaagcttc atttgtatta | 780 | |
| ttgtaaccat ttagacaagc taaatccttt ttattattgt ccttattgat tttatccaga | 840 | |
| ttaccgtatc taaagagcga tcaacagaaa aacggctgat tttagaccaa agtttcacaa | 900 | |
| actacatttg catgaacgtc atatatatat aaaccttgac ttttcttttt tttttttttt | 960 | |
| tttttttttc attatcaatt aatacaatta ataacaaaa | 1000 | |

<210> SEQ ID NO 9
<211> LENGTH: 634
<212> TYPE: DNA
<213> ORGANISM: Rhizopus delemar

<400> SEQUENCE: 9

| | | |
|---|---|---|
| tcatttaat tacgcatttt catttactaa tttgttacat tttgataacg tcaataaatc | 60 | |
| ttctaatttc ttttgttctc aaacagttta cagttctatc ttttttttta ccacaatcaa | 120 | |
| ttctcaatat acaacatagc aaatgtgctt cagtaaattc attaaattct tttaaaaaaa | 180 | |
| ggtaatttgt agcataaaat tcgactttat tgacgttttt tttatgatca tatacaaata | 240 | |
| aaatagttgc gaatgagaac taaatttttc attgttttta gtcatatcat ctggctgttg | 300 | |
| cacgatgatc gcagcatatt tttcttcaca acactcatcc tataagcacc tttcaggact | 360 | |
| ttcgtctgca ctttccatat ttgatttcat caattgattt gaattttat ccagtacaat | 420 | |
| ggtttgaatc tatacaataa attagtcaca gtataaaatt atgtctcatc ttgaacacac | 480 | |
| acctgcttaa caaagaaatg aagcactcta tcaatagtaa atacaatata tgcatcgatg | 540 | |
| ccaaatatat atcgtacatt ctcttcaaac gtagcttgat ctaaatcgcc atcaataaac | 600 | |
| ctttcaatca tcctcactag tgcattataa tggc | 634 | |

<210> SEQ ID NO 10
<211> LENGTH: 29
<212> TYPE: DNA
<213> ORGANISM: Artificial
<220> FEATURE:
<223> OTHER INFORMATION: Synthetic oligonucleotide

<400> SEQUENCE: 10

| | | |
|---|---|---|
| tagagggaaa aagagagaat tgaaatagg | 29 | |

<210> SEQ ID NO 11
<211> LENGTH: 31
<212> TYPE: DNA
<213> ORGANISM: Artificial
<220> FEATURE:
<223> OTHER INFORMATION: Synthetic oligonucleotide

<400> SEQUENCE: 11

| | | |
|---|---|---|
| ttttgttatt taattgtatt aattgataat g | 31 | |

<210> SEQ ID NO 12
<211> LENGTH: 36
<212> TYPE: DNA
<213> ORGANISM: Artificial
<220> FEATURE:
<223> OTHER INFORMATION: Synthetic oligonucleotide

<400> SEQUENCE: 12
aattaaataa caaaatcatt ttaattacgc attttc        36

<210> SEQ ID NO 13
<211> LENGTH: 37
<212> TYPE: DNA
<213> ORGANISM: Artificial
<220> FEATURE:
<223> OTHER INFORMATION: Synthetic oligonucleotide

<400> SEQUENCE: 13
catgattacg cggccgcgcc attataatgc actagtg        37

<210> SEQ ID NO 14
<211> LENGTH: 38
<212> TYPE: DNA
<213> ORGANISM: Artificial
<220> FEATURE:
<223> OTHER INFORMATION: Synthetic oligonucleotide

<400> SEQUENCE: 14 ctcttttttcc ctctaatgag aggcaaaatg aagcgtac        38

<210> SEQ ID NO 15
<211> LENGTH: 44
<212> TYPE: DNA
<213> ORGANISM: Artificial
<220> FEATURE:
<223> OTHER INFORMATION: Synthetic oligonucleotide

<400> SEQUENCE: 15
aattaaataa caaaatgtc ttctatcgaa acctccaaaa tctc        44

<210> SEQ ID NO 16
<211> LENGTH: 42
<212> TYPE: DNA
<213> ORGANISM: Artificial
<220> FEATURE:
<223> OTHER INFORMATION: Synthetic oligonucleotide

<400> SEQUENCE: 16
aattaaataa caaaatgga acgacgaat tcatccaata cc        42

<210> SEQ ID NO 17
<211> LENGTH: 44
<212> TYPE: DNA
<213> ORGANISM: Artificial
<220> FEATURE:
<223> OTHER INFORMATION: Synthetic oligonucleotide

<400> SEQUENCE: 17
gcgtaattaa aatgactatt ctggagagga ggcatttact ttac        44

<210> SEQ ID NO 18
<211> LENGTH: 50
<212> TYPE: DNA
<213> ORGANISM: Artificial
<220> FEATURE:
<223> OTHER INFORMATION: Synthetic oligonucleotide

<400> SEQUENCE: 18
tcattttaat tacgcatttt catttactaa tttgttacat tttgataacg        50

<210> SEQ ID NO 19
<211> LENGTH: 21
<212> TYPE: DNA

```
<213> ORGANISM: Artificial
<220> FEATURE:
<223> OTHER INFORMATION: Synthetic oligonucleotide

<400> SEQUENCE: 19
gttccttgct gtggatttgt g                                          21

<210> SEQ ID NO 20
<211> LENGTH: 24
<212> TYPE: DNA
<213> ORGANISM: Artificial
<220> FEATURE:
<223> OTHER INFORMATION: Synthetic oligonucleotide

<400> SEQUENCE: 20
gggtgtatct ctgtcctatt catg                                       24

<210> SEQ ID NO 21
<211> LENGTH: 771
<212> TYPE: DNA
<213> ORGANISM: Rhizopus delemar

<400> SEQUENCE: 21
atgggaaatt tggactttaa aatcaaattg gcaaatactt ttgccacttt gttcttggtt    60
agttctcaag gttttagctt ttctgggtgg ttcctgagtc attcttatga tttcggtccg   120
cgagatttcg caattatctt ggcaagtatc ttacactttt tacttattgg ctttactatc   180
tatcaatatt tgccaagctc acctaaagat gtttatgagg ctattggcta ttggtattta   240
ttaatagccg ttttgaacag tggtgtatca ttccttatgg attaccaagt taacttgttt   300
gctttcattg gacttctttg gcaagtagcg acactcgtct tcatctatca tcgttttcgt   360
gattatcctc ctcgcaatgg cacagatcat gcttttatca atgcgccctt ttccatttac   420
accgcttatt ctcttttttat tgttctctgg caagtattcc aatttagcga ccatacgaag   480
catagtcaaa ttgcacacgt gtttattata ctctttattg gttttatagc tcttcatttg   540
gttgattatt cacatcgaaa ggattgggtt tattcattaa caacagcatg gattcttttg   600
ggtgctgctg tattccttga tgatgctcca cacactgttt cacttatcgt agttggcgtt   660
cttataagcg cagtagcaag aacacttatt ccaaattggt tggagcgttt caacagaaga   720
tttagtcgtt gggcaaacag aataggtgaa agaacacctt tgctttcttg a            771

<210> SEQ ID NO 22
<211> LENGTH: 256
<212> TYPE: PRT
<213> ORGANISM: Rhizopus delemar

<400> SEQUENCE: 22

Met Gly Asn Leu Asp Phe Lys Ile Lys Leu Ala Asn Thr Phe Ala Thr
1               5                   10                  15

Leu Phe Leu Val Ser Ser Gln Gly Phe Ser Phe Ser Gly Trp Phe Leu
                20                  25                  30

Ser His Ser Tyr Asp Phe Gly Pro Arg Asp Phe Ala Ile Ile Leu Ala
            35                  40                  45

Ser Ile Leu His Phe Leu Leu Ile Gly Phe Thr Ile Tyr Gln Tyr Leu
        50                  55                  60

Pro Ser Ser Pro Lys Asp Val Tyr Glu Ala Ile Gly Tyr Trp Tyr Leu
65                  70                  75                  80

Leu Ile Ala Val Leu Asn Ser Gly Val Ser Phe Leu Trp Tyr Tyr Gln
                85                  90                  95
```

```
Val Asn Leu Phe Ala Phe Ile Gly Leu Leu Trp Gln Val Ala Thr Leu
            100                 105                 110

Val Phe Ile Tyr His Arg Phe Arg Asp Tyr Pro Pro Arg Asn Gly Thr
        115                 120                 125

Asp His Ala Phe Ile Asn Ala Pro Phe Ser Ile Tyr Thr Ala Tyr Ser
    130                 135                 140

Leu Phe Ile Val Leu Trp Gln Val Phe Gln Phe Ser Asp His Thr Lys
145                 150                 155                 160

His Ser Gln Ile Ala His Val Phe Ile Ile Leu Phe Ile Gly Phe Ile
                165                 170                 175

Ala Leu His Leu Val Asp Tyr Ser His Arg Lys Asp Trp Val Tyr Ser
            180                 185                 190

Leu Thr Thr Ala Trp Ile Leu Leu Gly Ala Ala Val Phe Leu Asp Asp
        195                 200                 205

Ala Pro His Thr Val Ser Leu Ile Val Val Gly Val Leu Ile Ser Ala
        210                 215                 220

Val Ala Arg Thr Leu Ile Pro Asn Trp Leu Glu Arg Phe Asn Arg Arg
225                 230                 235                 240

Phe Ser Arg Trp Ala Asn Arg Ile Gly Glu Arg Thr Pro Leu Leu Ser
                245                 250                 255

<210> SEQ ID NO 23
<211> LENGTH: 45
<212> TYPE: DNA
<213> ORGANISM: Artificial
<220> FEATURE:
<223> OTHER INFORMATION: Synthetic oligonucleotide

<400> SEQUENCE: 23
aattaaataa caaaaatggg aaatttggac tttaaaatca aattg                    45

<210> SEQ ID NO 24
<211> LENGTH: 41
<212> TYPE: DNA
<213> ORGANISM: Artificial
<220> FEATURE:
<223> OTHER INFORMATION: Synthetic oligonucleotide

<400> SEQUENCE: 24
gcgtaattaa aatgatcaag aaagcaaagg tgttctttca c                        41
```